(12) United States Patent
Maiti et al.

(10) Patent No.: US 9,322,028 B1
(45) Date of Patent: Apr. 26, 2016

(54) UNIQUE NUCLEIC ACID PROMOTER FORMED FROM TWO OR MORE PROMOTER SEQUENCES

(71) Applicant: University of Kentucky Research Foundation, Lexington, KY (US)

(72) Inventors: Indu Maiti, Lexington, KY (US); Nrisingha Dey, Bhubaneswar (IN)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/270,031

(22) Filed: May 5, 2014

Related U.S. Application Data

(60) Provisional application No. 61/819,017, filed on May 3, 2013.

(51) Int. Cl.
C12N 15/82 (2006.01)

(52) U.S. Cl.
CPC .................... *C12N 15/8216* (2013.01)

(58) Field of Classification Search
None
See application file for complete search history.

(56) References Cited

U.S. PATENT DOCUMENTS

| | | | |
|---|---|---|---|
| 6,118,049 A | 9/2000 | Bestwick et al. | |
| 6,930,182 B1 * | 8/2005 | Maiti et al. | 536/24.1 |
| 7,052,905 B1 * | 5/2006 | Maiti et al. | 435/320.1 |

OTHER PUBLICATIONS

Kumar et al., PLoS ONE, 2011, vol. 6(9) pp. 1-15.*
Acharya, S., et al. (2013) Development of an intra-molecularly shuffled efficient chimeric plant promoter from plant infecting Mirabilis mosaic virus promoter sequence. J. Biotechnol., http://dx.doi.org/10.1016/j.jbiotec.2013.08.022.
Acharya, S., et al. (2013) Efficient chimeric plant promoters derived from plant infecting viral promoter sequences. Planta, DOI 10.1007/s00425-013-1973-2.
Bhattacharyya S, Dey N, Maiti IB (2002) Analysis of cis-sequence of subgenomic transcript promoter from the Figwort mosaic virus and comparison of promoter activity with the Cauliflower mosaic virus promoters in monocot and dicot cells. Virus Res 90: 47-62.
Bhullar S, Chakravarthy S, Advai S, Datta S, Pental D, et al. (2003) Strategies for development of functionally equivalent promoters with minimum sequence homology for transgene expression in plants: cis-elements in a novel DNA context versus domain swapping. Plant Physiol 132: 988-998.
Comai L, Moran P, Maslyar D (1990) Novel and useful properties of a chimeric plant promoter combining CaMV 35S and MAS elements. Plant Mol. Biol 15: 373-381.
Dey N, Maiti IB (1999) Structure and promoter/leader deletion analysis of mirabilis mosaic virus (MMV) full-length transcript promoter in transgenic plants. Plant Mol. Biol 40: 771-782.

Goodrich JA, Tjian R (2010) Modes of transcriptional regulation: Unexpected roles for core promoter recognition factors in cell-type-specific transcription and gene regulation. Nat Rev Genetics 11: 549-558.
Kumar D, Patro S, Ranjan R, Sahoo DK, Maiti IB, et al. (2011) Development of useful recombinant promoter and its expression analysis in different plant cells using Confocal Laser Scanning Microscopy. PLoS ONE 6(9): e24627.doi:10.1371/journal.pone.0024627.
Kumar D, Patro S, Ghosh J, Das A, Maiti IB, Dey N (2012) Development of a salicylic acid inducible minimal sub-genomic transcript promoter from Figwort mosaic virus with enhanced root-and leaf-activity using TGACG motif rearrangement. Gene 503: 36-47.
Lee LY, Konov ME, Bassuner B, Frame BR, Wank K, et al. (2007) Novel Plant Transformation Vectors Containing the Superpromoter. Plant Physiol 145: 1294-1300.
Maiti IB, Gowda S, Kiernan J, Ghosh SK, Shepherd RJ (1997) Promoter/leader deletion analysis and plant expression vectors with Figwort Mosaic Virus (FMV) full-length transcript (Flt) promoter containing single and double enhancer domains. Transgenic Res 6: 143-156.
Ni M, Cui D, Einstein J, Narasimhulu S, Vergara CE (1995) Strength and tissue specificity of chimeric promoters derived from the octopine and mannopine synthase genes. The Plant J 7: 661-676.
Ranjan R, Patro S, Kumari S, Kumar D, Dey N, et al. (2011) Efficient chimeric promoters derived from full-length and sub-genomic transcript promoters of Figwort mosaic virus (FMV). Journal of Biotechnology 152: 58-62.
Rushton PJ, Reinstadler A, Lipka V, Lippok B, Somssich IE (2002) Synthetic plant promoters containing defined regulatory elements provides novel insights into pathogen-and wound-induced signaling. Plant Cell 14: 749-762.
Venter M (2007) Synthetic Promoters: genetic control through cis engineering. Trends in Plant Sci 12: 118-124.
Venter M, Botha FC (2010) Synthetic promoter engineering. In Plant Developmental Biology—Biotechnological Perspective Pua E-C, Davey MR, eds. Springer-Verlag Berlin Heidelberg 2: 393-414.
Ranjan R., et al. (2012) Development and Functional Analysis of Novel Genetic Promoters Using DNA Shuffling, Hybridization and a Combination Thereof. PloS ONE 7(3): e31931. doi:10.1371/journal.pone.0031931.
Banerjee, J et al. (2013) An Intergenic Region Shared by At4g35985 and At4g35987 in Arabidopsis thaliana Is a Tissue Specific and Stress Inducible Bidirectional Promotor Analyzed in Transgenic Arabidopsis and Tobacco Plants. PloS ONE 8(11): e79622. doi:10.1371/journal.pone.0079622.
Sahoo, D K et al. (2014) Analysis of Dahlia Mosaic Virus Full-length Transcript Promoter-Driven Gene Expression in Transgenic Plants. Plant Mol Biol Rep, vol. 32(3), DOI 10.1007/s11105-014-07389-9.
Sahoo, D K et al. (2014) pSiM24 Is a Novel Versatile Gene Expression Vector for Transient Assays As Well As Stable Expression of Foreign Genes in Plants. PloS ONE 9(6): e98988. doi:10.1371/journal.pone.0098988.

* cited by examiner

*Primary Examiner* — Michele K Joike
*Assistant Examiner* — Mindy G Brown
(74) *Attorney, Agent, or Firm* — Stites & Harbison PLLC; Mandy Wilson Decker

(57) ABSTRACT

Non-naturally occurring DNA promoters, include MSGT-PFlt, PFlt-UAS-2X and FSgt-PFlt. The MSGT-PFlt was developed and has expression shown to be equivalent to that of CaMV35S promoter. DNA promoters PFlt-UAS-2X and FSgt-PFlt were developed and tested in transient and transgenic system and found to be stronger than the CaMV35S promoter.

4 Claims, 23 Drawing Sheets

FIGURE 1

Sequence ID No 1: DNA Sequence of promoter clone PFlt-UAS-1X, 376-bp, (coordinate in respect of transcription start site, TSS, -352 to +24)

```
AGTTTTTACT TCGGACAGTC AAAAATGAGT TTAACTTCTC AGCCGAGGTA AAACAAGAAA TATGCTTACG TCTACAGAGG
GATTTCTCTG AAGATCATGT TGCCAGCTA  TGCGAACAAT CATCGGGAGA CTTGAGCCA  TCAAAGAGG  AGTGATGTAG
ACCTAAAGCA ATAATGGAGC CATGACGTAA GGGCTTACGC CCATACGAAA TAATTAAAGG CTGATGTGAC CTGTCGGTCT
CTCAGAACCT TTACTTTTTA TATTTGGCGT GTATTTTTAA ATTTCCACGG CAATGACGAT GTGACCTGTG CATCCGCTTT
GCCTATAAAT AAGTTTTAGT TTGTATTGAT CGACACGATC GAGAAGACAC GGCCAT
```

Sequence ID No 2: DNA Sequence of promoter clone PFlt-UAS-2X, 686-bp; coordinate in respect of transcription start site (TSS) -662 to +24

```
AGTTTTTACT TCGGACAGTC AAAAATGAGT TTAACTTCTC AGCCGAGGTA AAACAAGAAA TATGCTTACG TCTACAGAGG
GATTTCTCTG AAGATCATGT TGCCAGCTAT GCGAACAATC ATCGGGAGAT CTTGAGCCAA TCAAAGAGGA GTGATGTAGA
CCTAAAGCAA TAATGGAGCC ATGACGTAAG GGCTTACGCC CATACGAAAT AATTAAAGGC TGATGTGACC TGTCGGTCTC
TCAGAACCTT TACTTTTTAT ATTTGGCGTG TATTTTTAAA TTTCCACGGC AATGACGAGG TGACCCAACG AGTTTTACT
TCGGACAGTC AAAAATGAGT TTAACTTCTC AGCCGAGGTA AAACAAGAAA TATGCTTACG TCTACAGAGG GATTTCTCTG
AAGATCATGT TGCCAGCTAA TGCGAACAAT CATCGGGAGA TCCTGAGCCA ATCAAAGAGG AGTGATGTAG ACCTAAAGCA
ATAATGGAGC CATGACGTAA GGGCTTACGC CCATACGAAA TAATTAAAGG CTGATGTGAC CTGTCGGTCT CTCAGAACCT
TTACTTTTTA TATTTGGCGT GTATTTTTAA ATTTCCACGG CAATGACGAT GTGGCCTGTG CATCCGCTTT GCCTATAAAT
AAGTTTTAGT TTGTATTGAT CGACACGATC GAGAAGACAC GGCCAT
```

Sequence ID No 3: DNA Sequence of promoter clone FSgt-PFlt, 593-bp, coordinate in respect of transcription start site (TSS): -569 to +24

```
TTACAGTAAG AACTGATAAC AAAAATTTTA CTTATTTCCT TAGAATTAAT CTTAAAGGTG ATAGTAAACA AGGACGATTA
GTCCGTTGGC AAAATTTGGTT CAGCAGTAT CAATTTGATG TCGAACATCT TGAAGGTGTA AAAAACGTTT TAGCAGATTG
CCTCACGAGA GATTTTAATG CTTAAAAACG TAAGCGCTGA CGTATGATTT CCCAACGAGT TTTTACTTCG GACAGTCAAA
AATGAGTTTA ACTTCTCAGC CGAGGTAAAA CAAGAAATAT GCTTACGTCT ACAGAGGGAT TTCTCTGAAG ATCATGTTTG
CCAGCAATGC GAACAATCAT CGGGAGATCC TGAGCCAATC AAAGAGGAGT GATGTAGACC TAAAGCAATA ATGGAGCCAT
GACGTAAGGG CTTACGCCCA TACGAAATAA TGAAGGCTG  ATGTGACCTG TCGGTCTCTC AGAACCTTTA CTTTTTATAT
TTGGCGTGTA TTTTTAAATT TCCACGGCAA TGACGATGTG GCCTGTGCAT CCGCTTTGCC TATAAATAAG TTTTAGTTTG
TATTGATCGA CACGATCGAG AAGACACGGC CAT
```

FIGURE 9

Sequence ID No 4: DNA Sequence of promoter clone MSgt-PFlt

```
CGGTAAAACA GGTGATTACT AAATTTAGTA TTTATCTAAC CCCTGTTTGT TTTACAGTCA GGACAGATAA
TGTAAATCTT TTAAAAGGAT TTATGAATAA AAAGATTACT GGTGACAGTA AACAGGGAAG GCTAATAAGA
TGGCAAATGT GGTTTTCACA TTACACCTTT AAGGTGGACC ACCTAAAAGG AGAACAAAAT GTGCTGGCTG
ATTATCTCAC CAGAGAATTC CCCCAACGAG TTTTTACTTC GGACAGTCAA AAATGAGTTT AACTTCTCAG
CCGAGGTAAA ACAAGAAATA TGCTTACGTC TACAGAGGGA TTTCTCTGAA GATCATGTTT GCCAGCAATG
CGAACAATCA TCGGGAGATC CTGAGCCAAT CAAAGAGGAG TGATGTAGAC CTAAAGCAAT AATGGAGCCA
TGACGTAAGG GCTTACGCCC ATACGAAATA ATTAAAGGCT GTCGGTCTCT CAGAACCTTT
ACTTTTTATA TTTGGCGTGT ATTTTTAAAT TTCCACGGCA GATGTGACCT GGCCTGTGCA TCCGCTTTGC
CTATAAATAA GTTTTAGTTT GTATTGATCG ACACGATCGA ATGACGATGT
                                              GAAGACACGG CCAT
```

Sequence ID No 5: DNA Sequence of PFlt promoter fragment

```
AGTTTTTACT TCGGACAGTC AAAAATGAGT TTAACTTCTC AGCCGAGGTA AAACAAGAAA TATGCTTACG
TCTACAGAGG GATTTCTCTG AAGATCATGT TTGCCAGCTA TGCGAACAAT CATCGGGAGA TCTTGAGCCA
ATCAAAGAGG AGTGATGTAG ACCTAAAGCA ATAATGGAGC CATGACGTAA GGGCTTACGC CCATACGAAA
TAATTAAAGG CTGATGTGAC CTGTCGGTCT CTCAGAACCT TTACTTTTTA TATTTGGCGT GTATTTTTAA
ATTTCCACGG CAATGACGAT GTGACCTGTG CATCCGCTTT GCCTATAAAT AAGTTTTAGT TTGTATTGAT
CGACACGATC GAGAAGACAC GGCCAT
```

UNIQUE NUCLEIC ACID PROMOTER FORMED FROM TWO OR MORE PROMOTER SEQUENCES

CROSS-REFERENCE TO RELATED APPLICATION

This application claims the benefit of U.S. Provisional Patent Application No. 61/819,017, filed May 3, 2013, herein incorporated by reference.

FIELD OF THE INVENTION

The present application relates to DNA promoters for gene expression and in particular unique promoters formed from DNA fragments. Advantageously, the present promoter DNA has enhanced activity in terms of gene expression. The present invention also relates to methods for producing unique promoters.

BACKGROUND OF THE INVENTION

The key genetic regulator, promoter, usually determines the ultimate fate of gene transcription. The structure of eukaryotic promoter is modular comprising a distal upstream activating sequence (UAS) and a proximal core promoter containing TATA element. Both distal and proximal regions are embedded with a number of cis elements which acts as the binding sites of different transcription factors and transcription binding proteins (TBPs) while RNA polymerase binds to the proximity of TATA box. The combinatorial/spatial interactions between cis and trans factor along with the cross talk between the proximal and distal part of promoter usually determines the functional characteristics of the promoter and regulate the gene transcription (Goodrich and Tjian, 2010; Lee and Young, 2000). Based upon these factors, redesigning of promoter structure by genetic manipulations could be possible to develop a better promoter with altered cis-profiles/cis-arrangements. Such 'tailor-promoter' usually holds better promise for developing plant of interest in comparison to the native promoter. Exchanging/swapping/shuffling the proximal and distal domains among different native (plant/animal) promoter sequences, one can develop unique recombinant promoter-module that manifest functional properties combining the features of both donating and receiving promoters (Venter and Botha, 2010; Bhullar et al., 2003; Venter, 2007). Several engineered/modified promoters were developed in recent past (Comai et al., 1990, Ni et al., 1995; Lee et al., 2007; Rushton et al., 2002; Venter, 2007). The present inventors have developed several useful plant promoters using both full-length transcript (Flt-) and sub-genomic transcript (Sgt-) promoters from different members of pararetrovirus (Kumar et al., 2011; Ranjan et al., 2012; Patro et al., 2012, Kumar et al., 2012). Unfortunately, the availability of such engineered promoters is not sufficient to meet their current demand in plant molecular biology and there is a constant shortage of such promoter in plant molecular biology.

Again, in eukaryotes a single gene requires a promoter for its expression. Therefore, during gene stacking or gene pyramiding, one needs to use multiple numbers of heterologous promoters for expression multiple numbers of genes. There is possibility of promoter sequence homology based genetic rearrangement/recombination in case of repeated use of same promoter for expressing multiple number of gene in plant cell. In such cases, use of different heterologous promoters could be advantageous over multiple use of same promoter as it was documented that homologous sequences, more than 90 bp between two promoters often lead to gene silencing in transgenic plants (Flavell, 1994).

SUMMARY OF THE INVENTION

The present invention relates to unique, non-naturally (i.e. not found in nature) occurring promoters produced from fragments or full sequences of promoters from genomes of PFlt-UAS-2X and FSgt-PFlt from Peanut Chlortic Streak Virus (PC1SV) and Figwort Mosaic Virus (FMV) as well as MSgt-PFlt from genomes of the Peanut Chlortic Streak Virus (PC1SV) and Mirabilis Mosaic Virus (MMV). In addition, promoters in accordance with the disclosure include combinations of the aforementioned fragments. The present invention also relates to method for producing aforementioned non-naturally occurring promoters.

In accordance with this disclosure, an engineered genetic promoter DNA fragments obtained from Peanut Chlortic Streak Virus (PC1SV) and Figwort Mosaic Virus (FMV) includes promoters (i) PFlt-UAS-2X: developed by inserting an additional copy of a sub genomic transcript promoter fragment (−352 to −49) of Peanut Chlortic Streak Virus (PC1SV-Sgt) to the 5' end of TATA containing PC1SV-Flt promoter fragment between coordinates −352 to +24 and (ii) FSgt-PFlt: constructed by ligating a sub genomic transcript promoter fragment (−270 to −60) of Figwort Mosaic Virus (FMV-Sgt) to the 5' end of a PC1SV-Flt promoter fragment between coordinates −352 to +24.

This disclosure includes a technique for obtaining genetic promoters DNA fragments from Figwort Mosaic Virus (FMV) comprising isolating FMV Sgt promoters plus UAS domain of full length transcript of Peanut Chlortic Streak Virus (PC1SV). Further, this disclosure includes methods of assaying promoter activities subjecting to the isolation PFlt-UAS-2X and FSgt-PFlt promoters of Peanut Chlortic Streak Virus (PC1SV) and Figwort Mosaic Virus (FMV) Sgt promoters to the step of molecular cloning and determining the activities of the promoters both in transient and transgenic assay.

Further, the disclosure provides a technique for enhancing the activity of genetic promoter fragment.

The engineered promoters include PFlt-UAS-2X and FSgt-PFlt with higher efficacy of successful gene transformation in plant. The 305 bp long UAS domain of full-length transcript promoter fragment (−353 to −49) of Peanut Chlortic Streak Virus (PC1SV-Flt) was inserted at the 5' end of TATA containing PC1SV-Flt promoter fragment (−352 to +24) to develop 686 bp long full length transcript promoter fragment of Peanut Chlortic Streak Virus with double enhancer domain PFlt-UAS-2X. Likewise, a 211 bp long UAS domain of Figwort Mosaic Virus sub genomic transcript promoter fragment (−270 to −60) was ligated to the 5' end of a PC1SV-Flt promoter fragment between coordinates −352 to +24 to develop a recombinant promoter of 593 bp long FSgt-PFlt.

The inventors have evaluated the transient activities of these two newly derived promoter fragments; PFlt-UAS-2X and FSgt-PFlt in tobacco protoplast system along with their transgenic activities were tested in transgenic tobacco plants. The inventors have compared their transient and transgenic activities with that of the CaMV35S promoter and also observed positive correlation among the GUS activities of transgenic tobacco plant expressing PFlt-UAS-2X and FSgt-PFlt promoter separately with the accumulation level of corresponding uidA transcript in transgenic plant. Histochemical staining of different parts of transgenic plant expressing PFlt-UAS-2X and FSgt-PFlt promoter construct individually confirms that they are semi-constitutive in nature. Taken all together, the newly derived pararetrovirus based recombinant sub-genomic transcript promoters; PFlt-UAS-2X and FSgt-PFlt are additional molecular tools for transgenic plant development with much higher efficacy than the CaMV35S promoter. Thus they could become potential candidate-promoter for multi-gene based molecular pharming and plant metabolic engineering.

In addition, the present invention relates to an engineered genetic promoter DNA fragment obtained from Peanut Chlortic Streak Virus (PC1SV) and Mirabilis Mosaic Virus (MMV) wherein the promoter, MSgt-PFlt, constructed by ligating a sub genomic transcript promoter fragment (−356 to −125) of Mirabilis Mosaic Virus (MMV-Sgt) to the 5' end of a PC1SV-Flt promoter fragment between coordinates −352 to +24 (PFlt-UAS-1X).

The present invention also relates to a technique for obtaining genetic promoter DNA fragment from Mirabilis Mosaic Virus (MMV) comprising isolating MMV Sgt promoter plus UAS domain of full-length transcript of Peanut Chlortic Streak Virus (PC1SV). This invention also relates to methods of assaying promoter activities subjecting isolation of the MSgt-PFlt promoter from Peanut Chlortic Streak Virus (PC1SV) and Mirabilis Mosaic Virus (MMV) Sgt promoters to the steps of molecular cloning and determining the activities of the promoter both in transient and transgenic assay.

Further, the present invention relates to expression of immunological gene and immunological gene of interest in plant protoplast using engineered promoters, e.g. PFlt-UAS-2X and FSgt-PFlt and MSgt-PFlt.

As will be clear from the following discussion, the present promoters allow for enhanced gene expression in plants.

The engineered promoter namely, MSgt-PFlt with complete heterogenous sequences and possess almost equal transcriptional activity to that of the most widely used promoter, the CaMV35S. A 232 bp long UAS domain of Mirabilis Mosaic Virus sub-genomic transcript promoter fragment (−356 to −125) was ligated to the 5' end of a PC1SV-Flt promoter fragment between coordinates −352 to +24 to develop the recombinant promoter MSgt-PFlt (614 bp). The transient activities of this newly derived promoter fragment were evaluated; MSgt-PFlt in tobacco protoplast system, along with transgenic activities tobacco plants. Furthermore, the inventors compared its transient and transgenic activities with that of the CaMV35S promoter. In this regard, the inventors have observed positive correlation among the average GUS activities obtained from transgenic tobacco plant expressing MSgt-PFlt with the accumulation level of corresponding uidA transcripts in transgenic plant. Histochemical staining of different parts of transgenic plant expressing the MSgt-PFlt promoter construct confirms that it is a semi-constitutive promoter. Taken all together, the newly derived pararetrovirus based recombinant sub-genomic transcript promoter; MSgt-PFlt can be additional molecular tool for transgenic plant development with equivalent efficacy with that of the CaMV35S promoter. The recombinant promoter, MSgt-PFlt, reported in the present invention could be used as an alternative of the CaMV35S in plant biology; thus, it could become a potential candidate-promoter for multi-gene based molecular pharming and plant metabolic engineering.

BRIEF DESCRIPTION OF THE DRAWINGS

FIG. 1 shows the DNA sequences, SEQ ID NOS: 1-3, of the promoter PFlt-UAS-1X, PFlt-UAS-2X and FSgt-PFlt with single enhancer domain of sub-genomic transcript of Figwort Mosaic Virus ligated to the full length transcript of Peanut Chlortic Streak Virus.

FIG. 2 includes schematic diagrams of gene expression cassettes for Pft-UAS-1X (A), PFlt-UAS-2X (B) and FSgt-PFlt (C) promoters respectively GUS-13 glucuronidase; Kan$^{r-}$ Kanamycin resistant gene.

FIG. 3 shows transient activities of CaMV3 5S, PFlt-UAS-1X, PFlt-UAS-2X and FSgt-PFlt promoters in tobacco protoplast system coupled to GUS reporter gene.

FIG. 4 shows green florescence obtained from ImaGene Green treated transformed protoplast expressing CaMV 35S, PFlt-UAS-1X, PFlt-UAS-2X and FSgt-PFlt (coupled to GUS reporter gene). Panel 1, Panel 2 and Panel 3 represent bright field images, green fluorescence images and superimposed images respectively obtained from transformed protoplast expressing above promoter constructs.

FIG. 5 shows the transgenic promoter activities of CaMV35S, PFlt-UAS-1X, PFlt-UAS-2X and FSgt-PFlt promoter coupled to GUS reporter gene. The data presented are means of five independent experiments with respective standard deviation. For each construct, eight to ten independent transgenic lines developed. Untransformed control (Wild), tissue extract from wild-type *N. tabacum* cv. SamsunNN.

FIG. 6 shows real-time PCR based quantitative estimation of GUS transcripts accumulation in transgenic plants expressing GUS under the control of CaMV35S, PFlt-UAS-1X, PFIt-UAS-2X and FSgt-PFlt promoters. The data presented as an average fold differences of GUS transcript with corresponding standard deviation of three independent experiments. Each bar represents 4.2 fold difference of uidA level in transgenic plants expressing above promoter constructs independently considering the accumulation of mRNA level by CaMV35S promoter a value of 1.

FIG. 7 shows expression of mammalian Interleukin 2 (IL-2) protein in tobacco protoplast under control of PFlt-UAS-1X, PFlt-UAS-2X and FSgt-PFlt promoter.

FIG. 8 shows images of X-Gluc staining (Histochemical analysis) leaf petiole cross section of 21 days old transgenic plants expressing GUS under the control of CaMV 35S, PFlt-UAS-2X and FSgt-PFlt promoters (details of assay discussed under Example 3).

FIG. 9 shows the DNA sequences for SEQ ID NOS: 4 and 5, in which SEQ ID NO: 4 is the DNA sequence of promoter clone MSgt-PFlt, in accordance with the present invention (i.e. the UAS domain of full length transcript promoter from Peanut Chlortic Streak Virus; PFlt promoter fragment and the newly derived promoter MSgt-PFlt) and SEQ ID NO: 5 is the DNA sequence of a PFlt promoter fragment, in accordance with the present invention.

FIG. 10 shows schematic diagrams of gene expression cassettes carrying PFlt promoter fragment (A) and MSgt-PFlt (B) promoters respectively coupled to GUS reporter gene; GUS-β glucuronidase; Kan$^{r-}$ Kanamycin resistant gene.

FIG. 11 shows transient activities of CaMV35S, PFlt promoter fragment and MSgt-PFlt promoters in tobacco protoplast system coupled to GUS reporter gene.

FIG. 12 shows green florescence obtained from ImaGene Green treated transformed protoplast expressing corresponding promoter as mentioned above. Panel 1, Panel 2 and Panel 3 represent bright field images, green fluorescence images and superimposed images respectively obtained from transformed protoplast expressing above promoter constructs.

FIG. 13 shows the transgenic promoter activities of CaMV35S, PFlt and MSgt-PFlt promoter coupled to GUS reporter gene. The data represented are means of five independent experiments with respective standard deviation. For each construct, eight to ten independent transgenic lines developed. Untransformed control (Wild), tissue extract from wild-type *Nicotiana tabacum* cv. SamsunNN.

FIG. 14 shows real-time PCR based quantitative estimation of GUS transcript accumulation in transgenic plants expressing GUS under the control of CaMV35S, PFlt promoter fragment and MSgt-PFlt promoters. The data presented as an average fold differences of GUS transcript with corresponding standard deviation of three independent experiments. Each bar represents fold difference of uidA level in transgenic plants expressing above promoter constructs independently considering the accumulation of GUS-mRNA level by CaMV3 5S promoter a value of 1.

Figure 19:
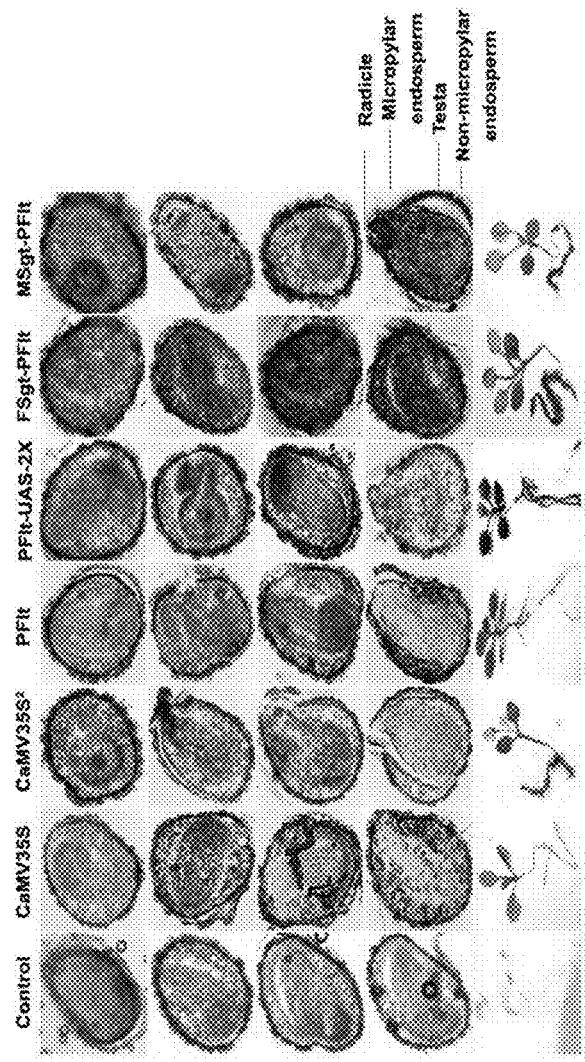

FIG. 19 are light microscope images/stains showing differential expression of the GUS reporter gene under control of CaMV35S, CaMV35S2, PFlt, PFlt-UAS-2X, FSgt-PFlt and MSgt-PFlt promoter constructs during different time-point of seed germination, which are light microscopy images of X-gluc treated whole seedlings (21 days) of untransformed control and transgenic tobacco plant expressing CaMV35S, CaMV35S2, PFlt, PFlt-UAS-2X, FSgt-PFlt and MSgt-PFlt promoters coupled to GUS reporter gene.

Figure 20:
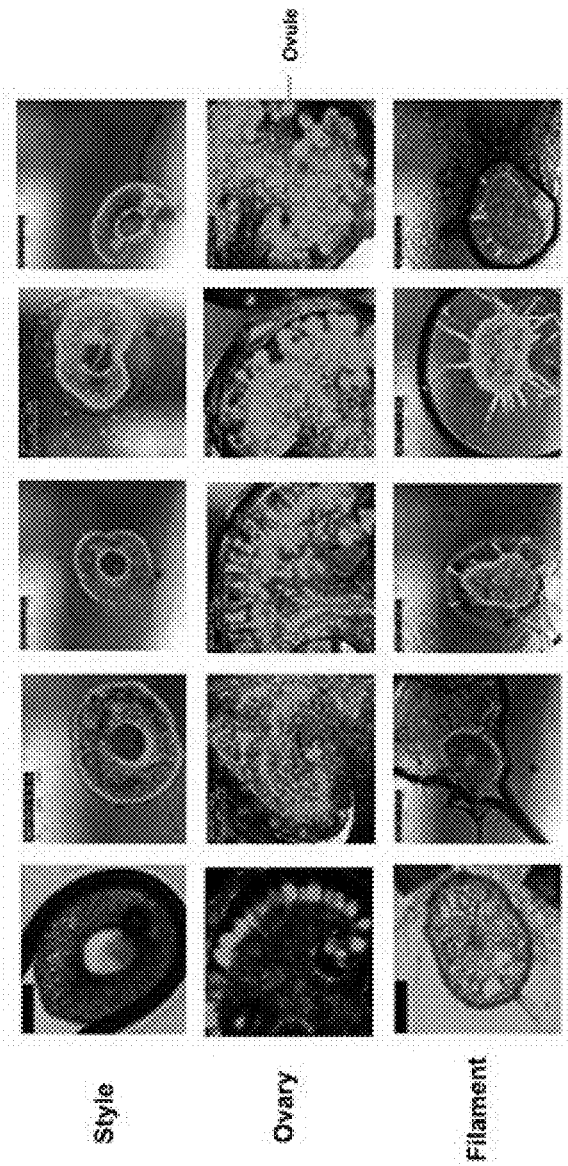

FIG. 20 are micrographs for CLSM based comparative analysis of the relative GUS expression under control of CaMV35S, PFlt, PFlt-UAS-2X, FSgt-PFlt and MSgt-PFlt promoter in transgenic floral organs, which are superimposed (bright field and fluorescent) images of ImaGene Green™ treated cross-sections of transgenic floral organ (style, ovary and filament) expressing the GUS gene under respective promoter construct.

Figure 21:
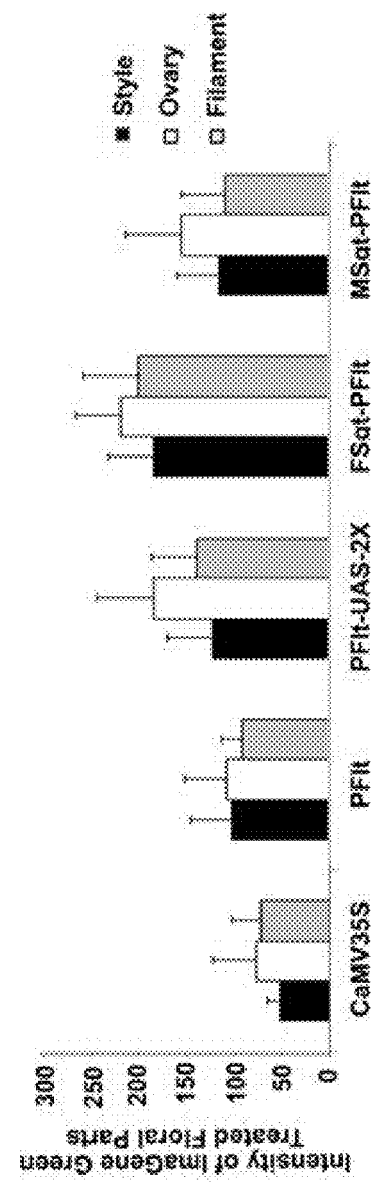

FIG. 21 is a graph showing intensities of Green fluorescence obtained from 50/60 regions of interest (ROIs) of transgenic floral organs expressing above promoter construct. The average intensity was determined for respective floral organs/tissues and presented.

Figure 22:
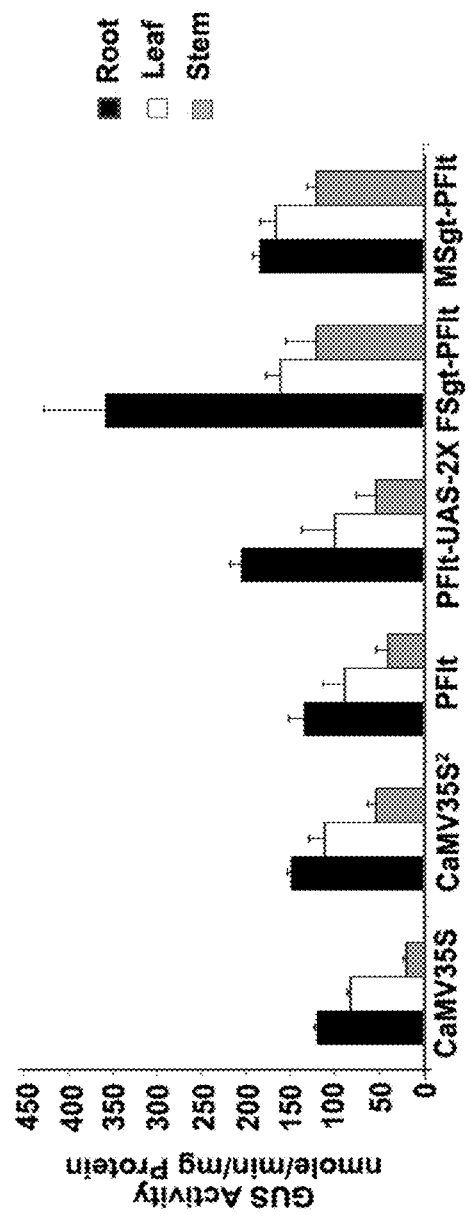

FIG. 22 is a graph showing average GUS activities (in nmole MU/min/mg protein) from the root, leaf and stem of transgenic tobacco seedling (21 days old) expressing GUS under the control of the above promoter constructs.

Figure 23:
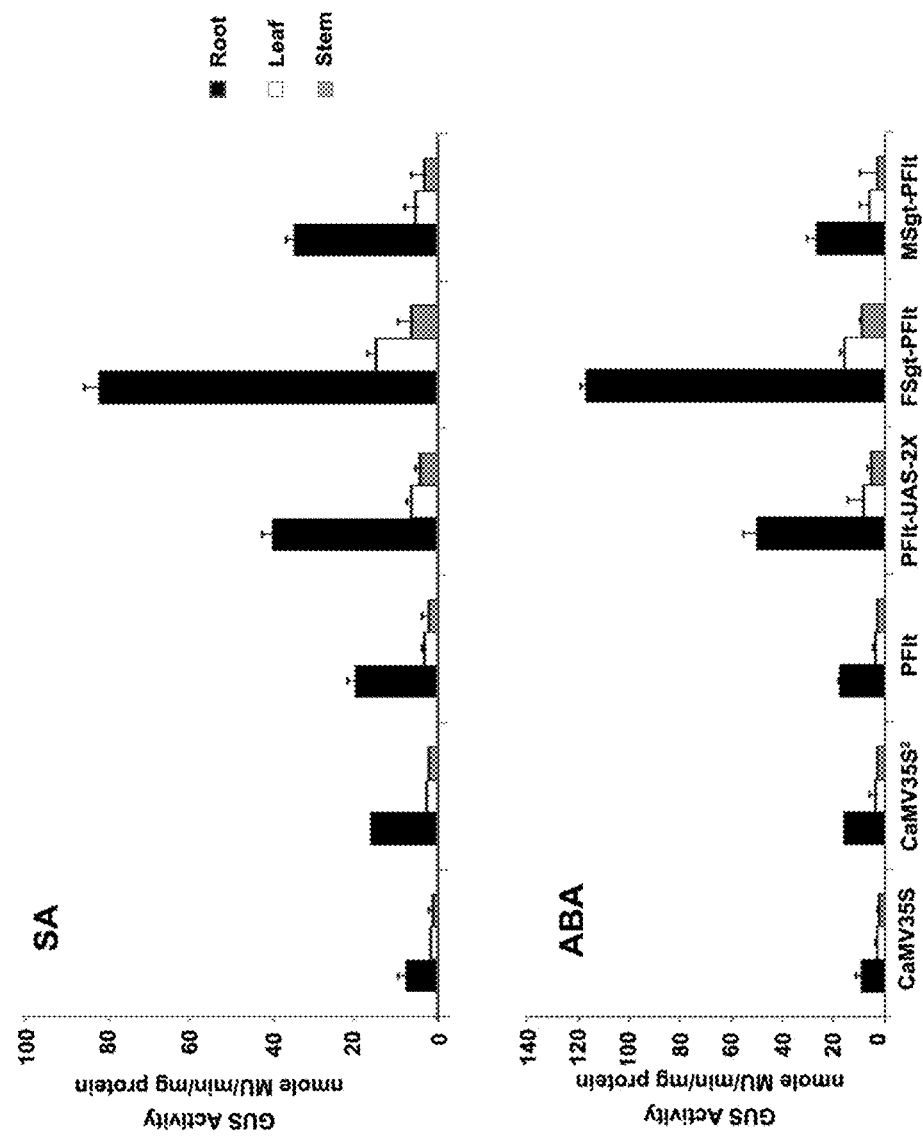

FIG. 23 are graphs showing spatial distribution of GUS expression (in nmole MU/min/mg protein) from the root, leaf and stem of 21 days old transgenic tobacco seedlings driven by CaMV35S, CaMV35S2, PFlt, PFlt-UAS-2X, FSgt-PFlt and MSgt-PFlt promoter constructs under 150 μM Salicylic Acid and Abscisic acid treatment.

DETAILED DESCRIPTION OF THE INVENTION

The present invention provides a strategy for construction of modified promoters; PFlt-UAS-2X and FSgt-PFlt employing prpmoter sequences from Peanut Chlortic Streak Virus and Figwort mosaic virus. This invention also relates to a method of using the promoters in plant and protoplast system for expression of any transgene. Features include:

Molecular cloning of PFlt-UAS-1X (PC1SV genomic coordinate 5725 to 6100, PC1SV-Flt promoter coordinates −352 to +24 from TSS) from Peanut Chlortic Streak Virus full-length transcript.

Molecular cloning of upstream activation sequence (PC1SV genomic coordinates 5725 to 6100, PC1SV promoter coordinates −352 to −49) from Peanut Chlortic Streak Virus full-length transcript (PFlt-UAS-1 X) promoter.

Molecular cloning of domain containing upstream activating sequence, from Figwort mosaic virus sub-genomic transcript (FMV-Sgt) promoter. (UAS from FMV genomic coordinates 5163 to 5363; FMV-Sgt promoter coordinates −270 to −60).

Construction of modified promoter (PFlt-UAS-2X) with double enhancer domain by adding the upstream activating sequence (promoter coordinates −352 to −49) to the 5' end of the core promoter domain (−352 to +24) of PC1SV Flt.

Construction of chimeric promoter (FPFlt-UAS-1X) by intermolecular hybridization by ligating the upstream activating sequence (−270 to −60) of Figwort mosaic virus to the core promoter domain (−352 to +24) of PC1SV Flt.

The efficacies of the modified promoters; (PFlt-UAS-2X) and chimeric promoter (FSgt-PFlt-UAS-1X) coupled to GUS reporter gene was tested by transient (in tobacco protoplast system) and transgenic (in tobacco plant) assays.

The modified PFlt-UAS-2X and chimeric promoters FSgt-PFlt were found to be stronger (4 to 6 fold) compared to the CaMV35S promoter widely used in plant biology.

The present invention also relates to a strategy for construction of modified promoter; MSgt-PFlt employing promoter sequences from Peanut Chlortic Streak Virus and Mirabilis Mosaic Virus. This invention also describes the method of using the said promoters in plant and protoplast system for expression of any transgene.

Additionally features include:

Molecular cloning of PFlt promoter fragment (PC1SV genomic coordinate 5725 to 6101, PC1 SV-Flt promoter coordinates −352 to +24 from TSS) from Peanut Chlortic Streak Virus full-length transcript.

Molecular cloning of domain containing upstream activating sequence, from Mirabilis Mosaic Virus sub-genomic transcript (MMV-Sgt) promoter. (UAS from MMV genomic coordinates; MMV-Sgt promoter coordinates −356 to −125).

Construction of recombinant promoter (MSgt-PFlt) by intermolecular hybridization of the upstream activating sequence (−356 to −125) of Mirabilis Mosaic Virus to the core promoter domain (−352 to +24) of PCISV Flt.

The efficacies of the modified promoter (MSgt-PFlt) coupled to GUS reporter gene was tested by transient (in tobacco protoplast system) and transgenic (in tobacco plant) assays.

The modified promoter, MSgt-PFlt was found to be comparable/equivalent to the CaMV35S promoter, most widely used promoter in plant biology.

EXAMPLES

The present invention will now be described with reference to the following non-limiting examples and experiments.

Example 1

Construction of Vector Containing Modified and Chimeric Promoter

1a) Cloning of Modified and Chimeric Promoter

The 376 bp long PFlt-UAS-1X promoter fragment (PC1SV-FLt; SEQ ID NO: 1, FIG. 1) (−352 to +24), 305 bp long PFlt-UAS-2X promoter fragment (−353 to −49) and 211 by long FMV-Sgt-UAS promoter fragment (−270 to −60) were PCR amplified as described by Dey and Maiti, (1999) using specific primer pairs containing the appropriate sequence to generate EcoRI and HincII sites at the 5' end and SmaI and HindIII sites at the 3' end using corresponding genomic DNA clone. PCR-amplified fragments were restricted with EcoRI and HindIII endonucleases and gel purified. Digested promoter fragments were cloned into the corresponding sites of pUC119 vector; the resulting plasmids were designated as pUCPFlt-UAS-1X, pUCPFlt-UAS-1X-UAS and pUCFSgt-UAS. All of these plasmids were subjected to automated sequencing. The PFlt-UAS-1X promoter fragment was isolated from pUCPFlt-UAS-1X clone as HincII-HindIII fragment; and it was then inserted into the SmaI and HindIII sites of pUCPFlt-UAS-1X-UAS clone and the resulting plasmid was designated as PFlt-UAS-2X. Similarly, the PFlt-UAS-1X promoter fragment (376-bp) was isolated from pUCPFlt-UAS-1X clone as HincII-HindIII fragment; and it was then inserted into the SmaI and HindIII sites of pUCFSgt-UAS clone. The resulting chimeric promoter clone was designated as FSgt-PFlt. The plasmids were sequenced (Sanger et al., 1977) and the sequence of this promoter is presented in FIG. 1, SEQ ID NO: 3.

1b) Cloning of PFlt-UAS-2X and FSgt-PFlt Promoter Sequence in the Protoplast Expression Vector pUCPMAGUS The PFlt-UAS-1X, PFlt-UAS-2X and FSgt-PFlt promoter was isolated as EcoRI and HindIII fragment from sequencing vectors pUCPFlt-UAS-1X, pUCPFlt-UAS-2X and pUCFSgt-PFlt respectively and sub-cloned into the corresponding sites of the protoplast expression vector coupled to GUS reporter gene pUCPMAGUS (Dey and Maiti 1999) by replacing the CaMV35S promoter and the resulting clones were designated as pUPPFlt-UAS-1X, pUPPFlt-UAS-2X and pUPFSgt-PFlt respectively.

2a) Cloning of Interleukin-2 (IL-2)

The 500 bp long IL-2 was PCR amplified using specific primer sequence to incorporate Xho I and XbaI in the 5' and 3' end of the amplified gene respectively. It was then cloned into the corresponding sites of pUC119 containing PFlt-UAS-1X, PFlt-UAS-2X and FSgt-PFlt promoters and the resulting plasmid was named as IL-2pUCPFlt-UAS-1X, IL-2pUCPFlt-UAS-2 and IL-2pUCF Sgt-PFlt respectively.

2b) Cloning of IL-2PFlt-UAS-1X, IL-2PFlt-UAS-2X and IL-2FSgt-PFlt in the Protoplast Expression Vector p UCPMAGUS The IL-2 gene was isolated as XhoI and XbaI fragment from sequencing vectors IL-2pUCPFlt-UAS-1X, IL-2pUCPFlt-UAS-2X and IL-2pUCFSgt-PFlt respectively and sub-cloned into the corresponding sites of the protoplast expression vector pUCPMAGUS (Dey and Maiti 1999) by replacing the CaMV35S promoter and the resulting clones were designated as IL-2pUPPFlt-UAS-1X, IL-2pUPPFlt-UAS-2X and IL-2pUPFSgt-PFlt respectively.

Example 2

Transient Assay of the Promoters in Tobacco Protoplast System

Protoplasts from tobacco cell suspension cultures (Xanthi 'Brad') were purified on 20% sucrose gradient after being digested by cellulase (Sigma Cat #C0615-1 G) and pectinase (Sigma Cat #P4300-5 KU). Electroporation of protoplasts with supercoiled DNA containing GUS reporter genes were conducted as described earlier (Kumar et al., 2012) by using the GenePulser II Apparatus (BioRad) with the Capacitance Extender II (Model 165-2107). In brief, an aliquot of 750-µl containing 2×106 protoplasts in an electroporation cuvette (0.4 cm electrode gap) was electroporated (200 V used for charging 965-µF capacitance for 40-50 ms) with 5-µg of each following promoter constructs CaMV35S, pUPPFlt-UAS-1X pUPPFlt-UAS-2X and pUPFSgt-PFlt.

Figure 2:
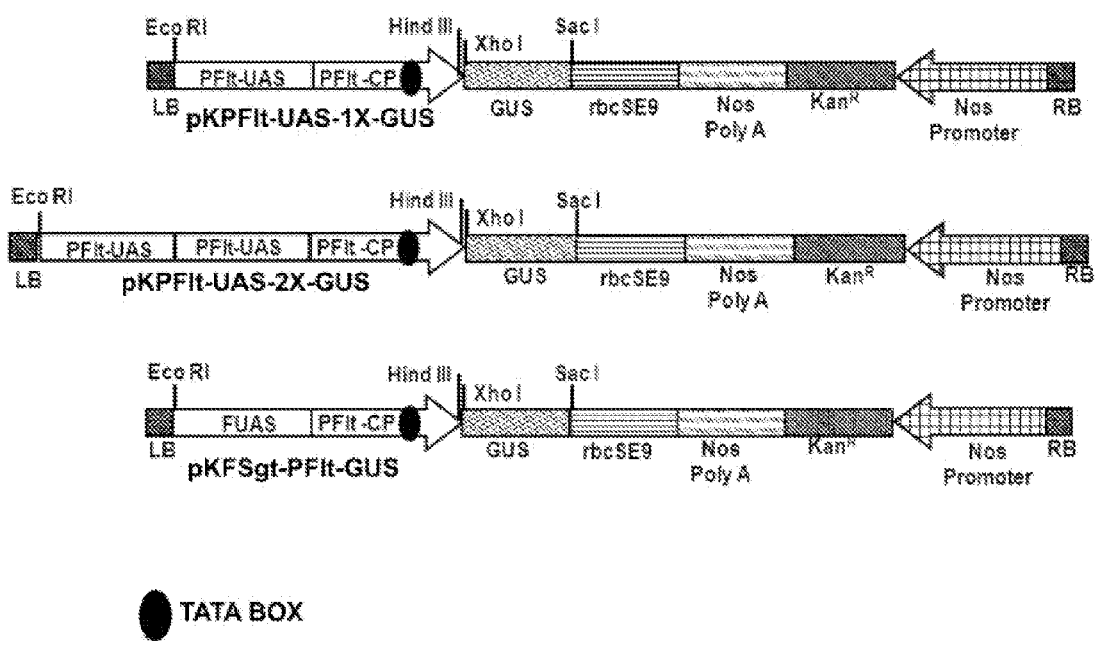
Figure 3:
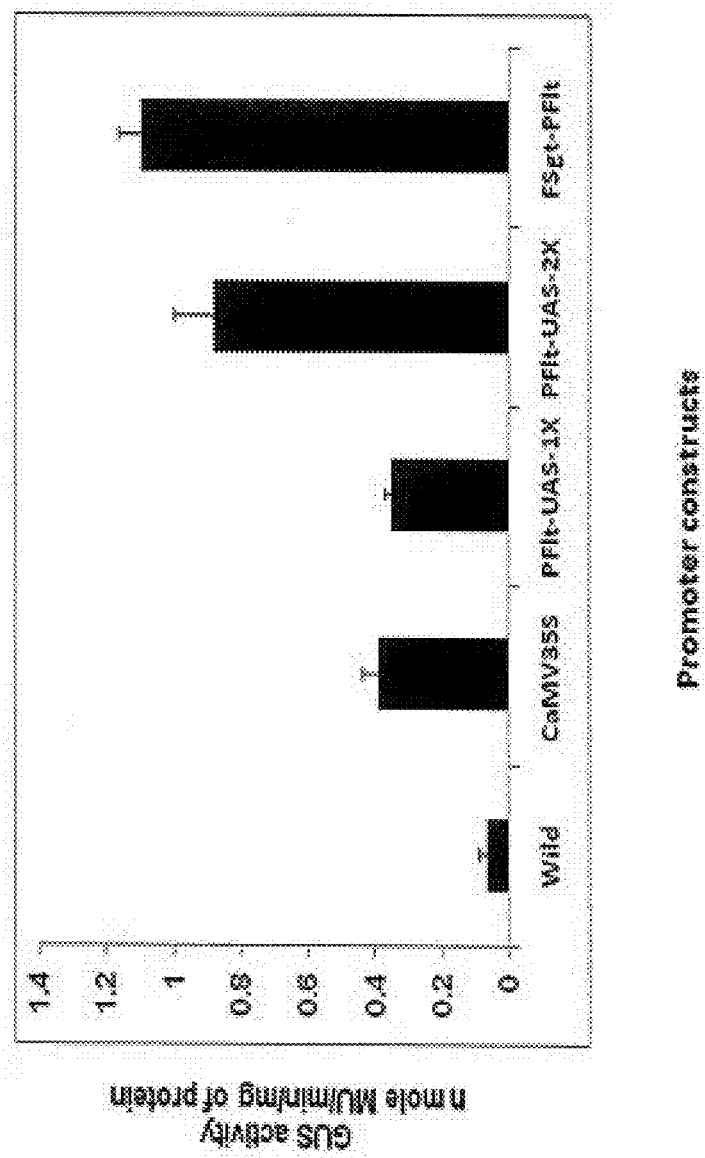

Transformed protoplast expressing CaMV35S, PFlt-UAS-1X, PFlt-UAS-2X and FSgt-PFlt were incubated in 1 mM MUG (4-methyl-umbelliferyl-D-glucuronide) at 37° C. for 30 min. to produce MU (7-Hydroxy-4-Methylcoumarin) for biochemical GUS estimation (Jefferson et al., 1987) and the result were presented in FIG. 3. pUPPFlt-UAS-2XGUS and pUPFSgt-PFlt-UAS-1XGUS promoter showed 2.25 and 3.6 times stronger activity compared to CaMV35S promoter in tobacco protoplast system.

Figure 4:
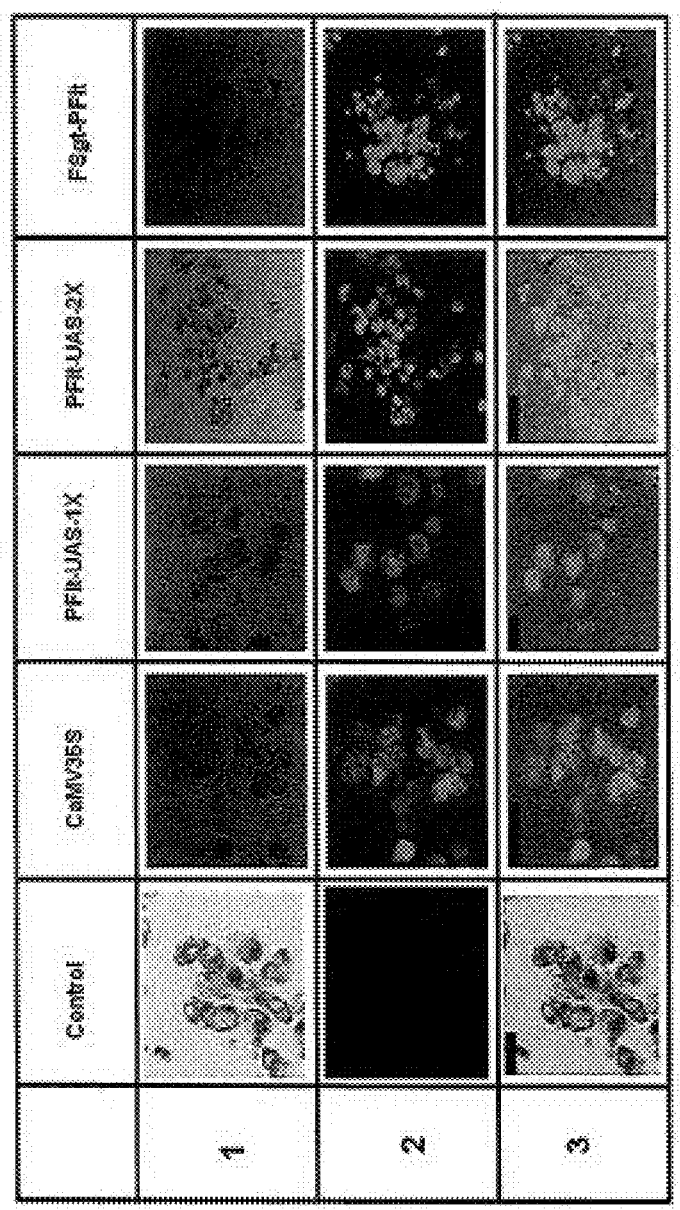

To confirm the reporter gene (GUS) expression, the transformed protoplast expressing CaMV35S, PFlt-UAS-1X, PFlt-UAS-2X and FSgt-PFlt promoter were incubated individually, in 55 mM ImaGene Green™ C12FDGlcU substrate (ImaGene Green™ GUS Gene Expression Kit; Invitrogen, Oregon, USA) as per kit's instructions and kept under vacuum infiltration for 10 min initially and then incubated at room temperature for 2-3 hrs in the dark. Fluorescence images of protoplast the transform with CaMV35S, PFlt-UAS-1X, PFlt-UAS-2X and FSgt-PFlt promoter constructs were captured using a CLSM (TCS SP5; Leica, D 68165 Mannheim, Germany). The captured fluorescence images were presented in FIG. 4. For estimating GUS, the ImaGene Green™ treated transformed protoplast were excited with 488 diode laser (use of 495 nm UV laser may be more appropriate) and fluorescence emissions were collected between 500 and 515 nm with detector (PMT) gain set at 1150V. GUS localizations at cellular/tissue level were detected by green fluorescent lipophilic fluorescein derivative (5-dodecanoy-laminofluorescein).

Figure 7:
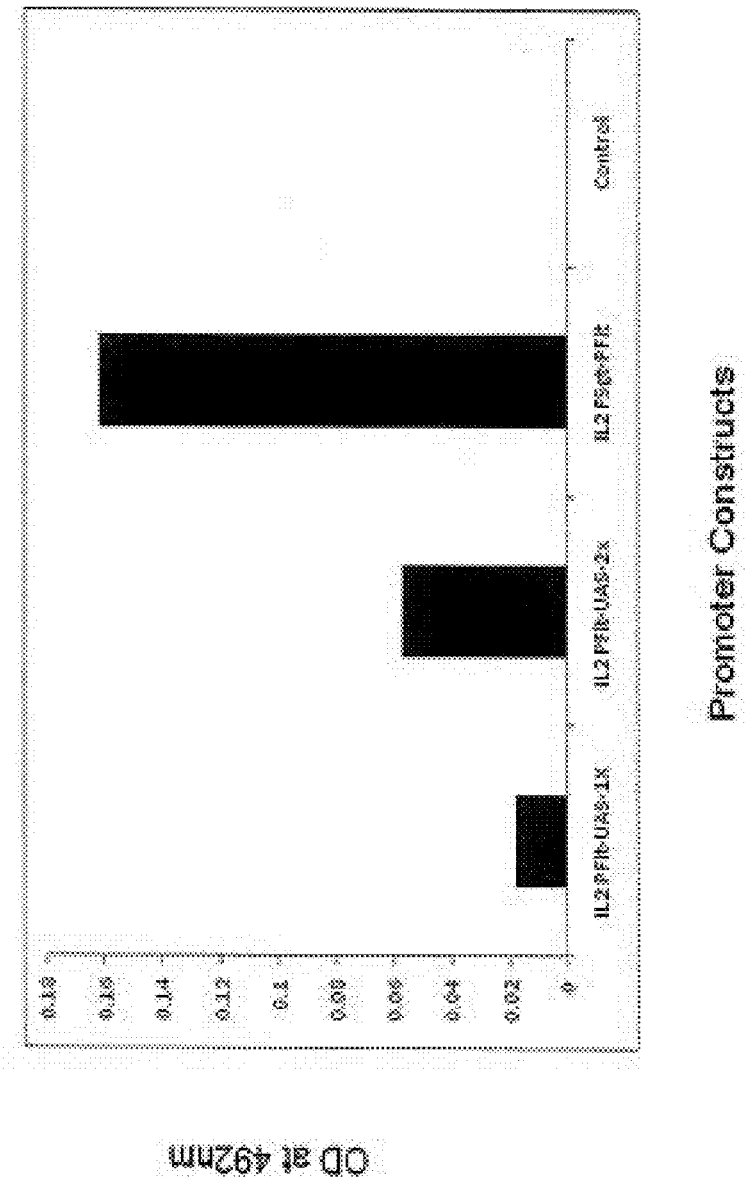

ELISA of Protoplast Derived IL-2 Protein Driven by PFlt-UAS-1X PFlt-UAS-2X and FSgt-PFlt Promoter Sequence A 100 µl PBS containing 10 µg of protein extracts from protoplasts transformed with each of IL-2pUPPFlt-UAS-1X, IL-2pUPPFlt-UAS-2X and IL-2pUPFSgt-PFlt constructs were coated into a 96 well ELISA plate. The concentration of protoplast derived IL-2 was estimated following indirect ELISA protocol (Vazquez et al., 1996) using an anti-IL2 antibody (Santacruz, USA) and the result obtained is presented in FIG. 7.

Example 3

Construction of Plant Expression Vectors with PFlt-UAS-1X, PFlt-UAS-2X and FSgt-PFlt Promoters, Plant Transformation and Analysis of Transgenic Plants Promoter fragment PFlt-UAS-1X (376 bp) (SEQ ID NO: 1), PFlt-UAS-2X (686 bp) (SEQ ID NO: 2) and FSgt-PFlt (593 bp) (SEQ ID NO: 3) (See FIG. 1) were purified from corresponding pUC-clones and were cloned into the plant expression vector pKYLX71GUS (Schardl et al., 1987; Dey and Maiti 1999) at its unique EcoRI and HindIII sites that flank the promoter by replacing the CaMV35S promoter. Resulting plant expression vectors were designated pKPFlt-UAS-1X, pKPFlt-UAS-2X and pKFSgt-PFlt respectively.

Figure 5:
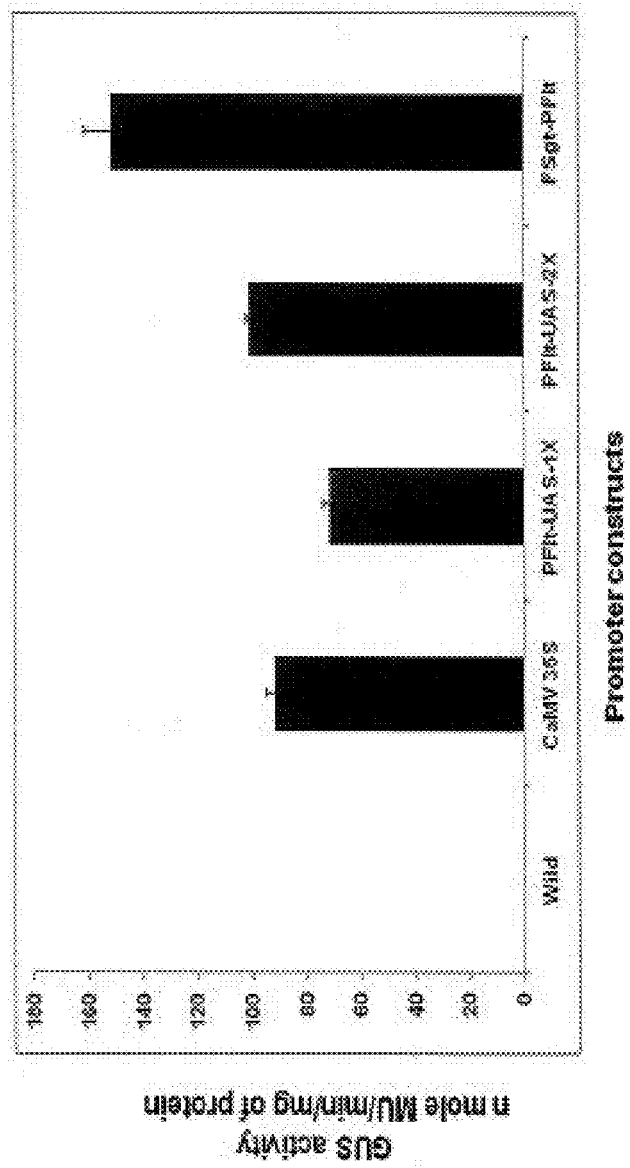

Promoter constructs namely pKYLX-GUS (containing CaMV35S promoter), pKPFlt-UAS-1X-GUS, pKPFlt-UAS-2X-GUS and pKFSgt-PFlt-GUS were introduced into *Agrobacterium tumefaciens* strain C58C1:Pgv3850 by freeze thaw method. Tobacco plants (*Nicotiana tabacum* cv Samsun NN) were transformed with the engineered *Agrobacterium* as described earlier (Maiti et al., 1993). About 10 (ten) independent plant lines were generated for each construct. Regenerated Kanamycin-resistant plants were grown under greenhouse conditions (Temp—28±2° C., humidity—60 to 70%) until setting of seed. Seeds were collected from mature plant and germinated on Kanamycin antibiotic 300 mg per liter. Analysis of GUS Expression in Transgenic Tobacco Plants Independent tobacco transgenic lines were developed using CaMV35S, PFlt-UAS-1X, PFlt-UAS-2X and FSgt-PFlt promoter as described earlier. Comparative GUS expression analyses were conducted using plant leaves (second from the top) extract following protocol of Jefferson et al., 1987. The result obtained was presented in FIG. 5. Transgenic plants expressing the PFlt-UAS-2X and FSgt-PFlt promoter showed 1.2 and 2 times stronger activity compared to the CaMV 35S promoter.

Figure 8:
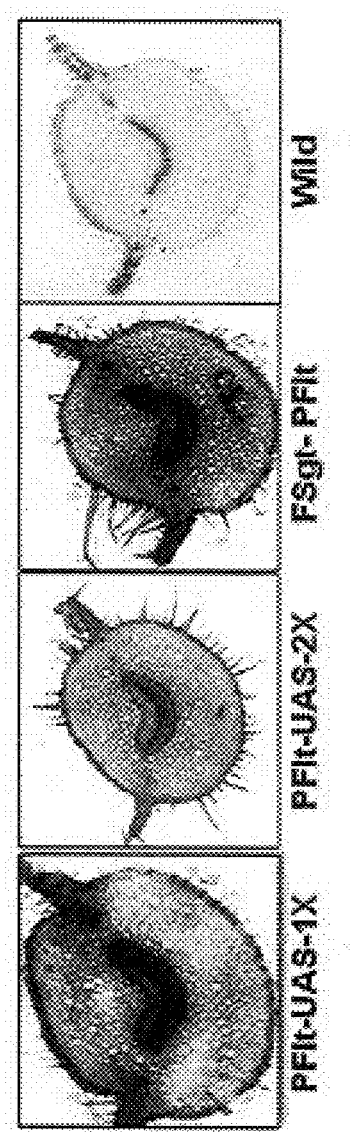
Figure 10:
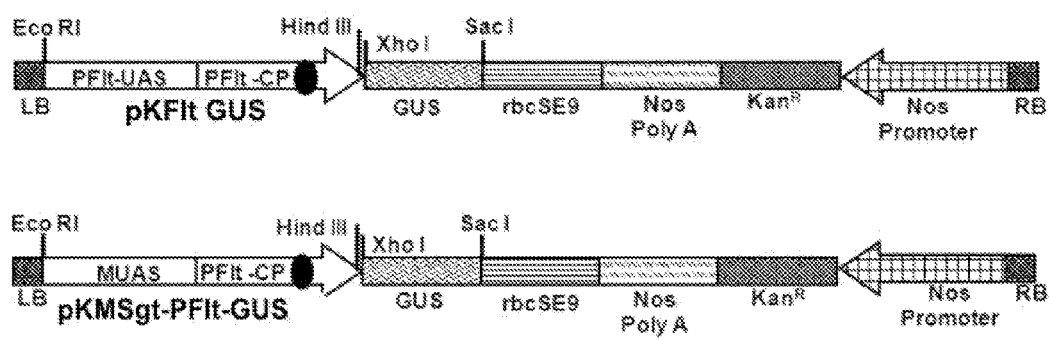

Transgenic plant sections expressing the GUS gene developed for each constructs were immersed into histochemical GUS staining buffer (100 mM $NaPO_4$, 0.5 mM $K_3[Fe(CN)_6]$, 0.5 mM $K_4[Fe(CN)_6]$, 10 mM EDTA, 1 mg/ml 5-bromo-4-chloro-3-indolyl-b-D-glucuronide (X-glue), vacuum infiltrated under pressure for 10 min followed by incubation at 37° C. for overnight. Samples were then washed and fixed (in 50% ethanol, 7% acetic acid). The intensity of color development in different tissues was monitored and photographs were taken by using inverted Leica DM LS2 microscope at 4× magnification (FIG. 8).

Example 4

Figure 6:
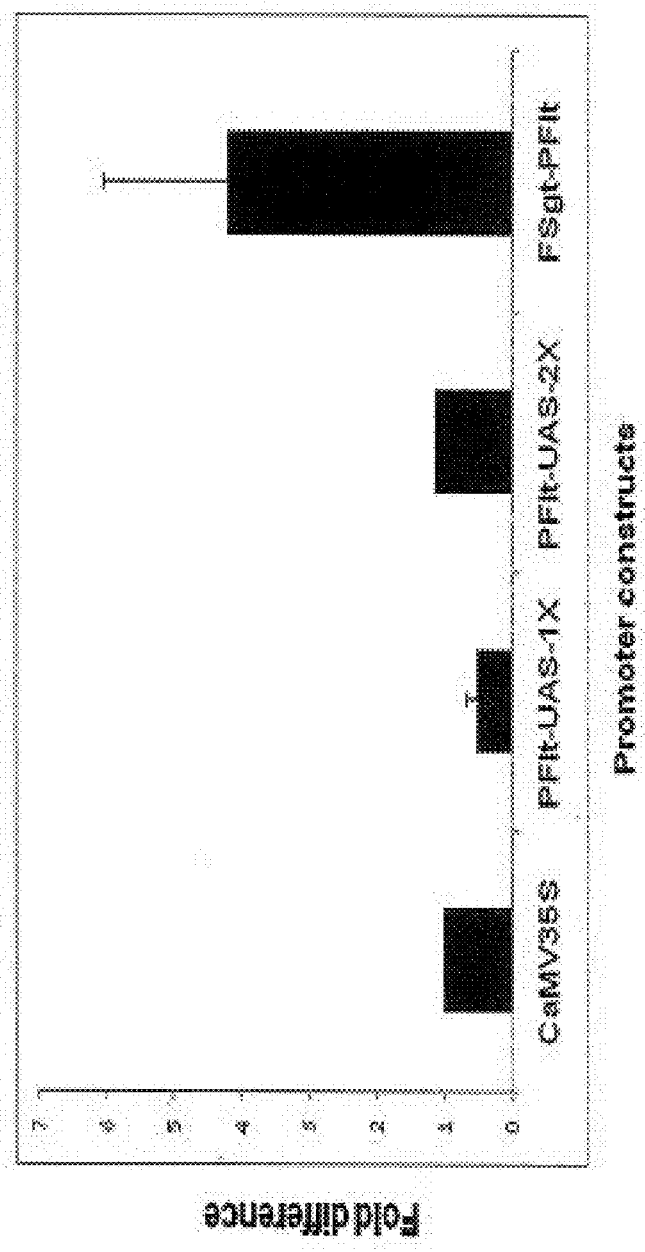

Reactions of qRT-PCR were performed as described earlier by Kumar et al., 2011. The cDNA was synthesized using RNA (DNaseI treated) isolated from transgenic tobacco plants expressing CaMV35S, PFlt-UAS-1X, PFlt-UAS-2X and FSgt-PFlt promoter constructs individually using cDNA synthesis Kit (Fermentas, USA). The qRT-PCR for relative expression analysis was performed using the corresponding cDNA template (1:15 dilution) and SYBR Premix Ex Takirm II (Perfect Real Time, Takara Bio Inc., Japan) employing Opticon-2 Real-time PCR machine (MJ Research, Bio-Rad; Model; CFD-3220). Gene specific primers for GUS were used at a concentration of 0.8 mmolar to get 95% efficiency. The absence of genomic DNA contamination was confirmed using minus-reverse-transcriptase controls. The Ct value for each reaction was obtained with the help of the software attached with the machine and fold changes in the transcript levels of each construct (considered for qRT-PCR) were presented (FIG. 6).

TABLE 1

Primer Sequences

| SEQ. NO. | Name of Constructs | Primer Sequence to amplify respective promoter in 5' to 3' direction |
|---|---|---|
| 6. | PFlt-UAS-1X (forward) | GCGGGCGAATTCGTCAACGAGTTTTTACTTCGGACA |
| 7. | PFlt-UAS-1X (reverse) | ATGCAGAAGCTTATGGCCGTGTCTTCTCGA |
| 8. | PFlt-UAS-2X (forward) | GCGGGCGAATTCGTCAACGAGTTTTTACTTCGGACA |
| 9. | PFlt-UAS-2X (reverse) | ATGCAGAAGCTTATGGCCGTGTCTTCTCGA |
| 10. | FSgt-PFlt (forward) | CCCGAATTCGTCGACTTTACAGTAAGAACTGATAACA |
| 11. | FSgt-PFlt (reverse) | ATGCAGAAGCTTATGGCCGTGTCTTCTCGA |
| 12. | GUS (real time) (forward) | GATCGCGAAAACTGTGGAAT |
| 13. | GUS (real time) (reverse) | TAATGAGTGACCGCATCGAA |
| 14. | Interleukin 2 (forward) | GCGGGCTCGAGAACCATGGGTTACAGCATGCAGCTCGCA |
| 15. | Interleukin 2 (reverse) | ATGCAGTCTAGATCAGTGATGGTGATGGTGATGTTGAGGGCTTGTTGAGAT |

Information for SEQ ID No: 1 (FIG. 1)
(i) Sequence characteristics: DNA (Genomic)
(ii) Molecule type: Recombinant DNA
(iii) Original source:
(A) Organism: Peanut Chlortic Streak Virus (PC1SV)
** This promoter DNA clone PFlt-UAS-1X is submitted to Microbial Type Culture Collection and Gene Bank (MTCC), Chandigarh, India under Budapest treaty.

Information for SEQ ID No: 2 (FIG. 1)
(iv) Sequence characteristics: DNA (Genomic)
(v) Molecule type: Recombinant DNA
(vi) Original source:
(A) Organism: Peanut Chlortic Streak Virus (PC1SV)
** This promoter DNA clone PFlt-UAS-2X is being submitted to Microbial Type Culture Collection and Gene Bank (MTCC), Chandigarh, India under the Budapest treaty. All restrictions to the deposit will be revoked upon allowance of a patent covering the subject matter and the deposit will be replenished be if needed.

Information for SEQ ID No: 3 (FIG. 1)
(vii) Sequence characteristics: DNA (Genomic)
(viii) Molecule type: Recombinant DNA
(ix) Original source:
(A) Organism: Peanut Chlortic Streak Virus (PC1SV) and Figwort mosaic caulimovirus (FMV).
** This promoter DNA clone FSgt-PFlt is being submitted to Microbial Type Culture Collection and Gene Bank (MTCC), Chandigarh, India under the Budapest treaty. All restrictions to the deposit will be revoked upon allowance of a patent covering the subject matter and the deposit will be replenished be if needed.

Example 5

Construction of Vector Containing Modified and Chimeric Promoter

1a) Cloning of Modified and Chimeric Promoter

The 376 bp long PFlt promoter fragment (−352 to +24) and 232 bp long MMV-Sgt promoter fragment (− 356 to −125) containing UAS domain were PCR amplified as described by Dey and Maiti, (1999) using specific primer pairs containing the appropriate sequence to generate EcoRI and HincII sites at the 5' end and SmaI and HindIII sites at the 3' end using corresponding genomic DNA clone. PCR-amplified fragments were restricted with EcoRI and HindIII endonucleases and gel purified. Digested promoter fragments were cloned into the corresponding sites of pUC119 vector; the resulting plasmids were designated as pUCPFlt promoter fragment and pUCMSgt-UAS. All of these plasmids were subjected to automated sequencing. The 376 bp long PFlt promoter fragment was isolated from pUCPFlt clone as HincII-HindIII fragment; and it was then inserted into the SmaI and HindIII sites of pUCMSgt-UAS clone. The resulting chimeric promoter clone was designated as MSgt-PFlt. The plasmids were sequenced (Sanger et al., 1977) and the sequence of this promoter is presented in FIG. 9.

1b) Cloning of MSgt-PFlt Promoter Sequence in the Protoplast Expression Vector pUCPMAGUS The PFlt promoter fragment and MSgt-PFlt promoter were isolated as EcoRI and HindIII fragments from corresponding pUC based clones as discussed above and sub-cloned into the corresponding sites of the protoplast expression vector coupled to GUS reporter gene pUCPMAGUS (Dey and Maiti 1999) by replacing the CaMV35S promoter and the resulting clones were designated as pUPPFlt and pUPMSgt-PFlt respectively.

2a) Cloning of IL-2 in the Protoplast Expression Vector Carrying PFlt and MSgt-PFlt Promoter Fragments.

The 500 bp long IL-2 gene was PCR amplified using specific primer sequence (Table 2) to incorporate Xho I and XbaI in the 5' and 3' end of the amplified gene respectively. The IL-2 gene was cloned into the corresponding sites of the protoplast expression vector (Dey and Maiti 1999) by replacing the CaMV35S promoter and the resulting clones were designated as pUPPFlt-IL-2 and pUPMSgt-PFlt-IL-2 respectively.

Example 6

Transient Assay of the Promoters in Tobacco Protoplast System

Protoplasts from tobacco cell suspension cultures (Xanthi 'Brad') were purified on 20% sucrose gradient after being digested by cellulase (Sigma Cat #C0615-1 G) and pectinase (Sigma Cat II P4300-5 KU). Electroporation of protoplasts with supercoiled DNA containing GUS reporter genes were conducted as described earlier (Kumar et al., 2012) by using the GenePulser II Apparatus (BioRad) with the Capacitance Extender II (Model 165-2107). In brief, an aliquot of 750-0 containing $2 \times 10^6$ protoplasts in an electroporation cuvette (0.4 cm electrode gap) was electroporated (200 V used for charging 965-μF capacitance for 40-50 ms) with 5-μg of each following promoter constructs CaMV35S, pUPPFlt and pUPMSgt-PFlt.

Figure 11:
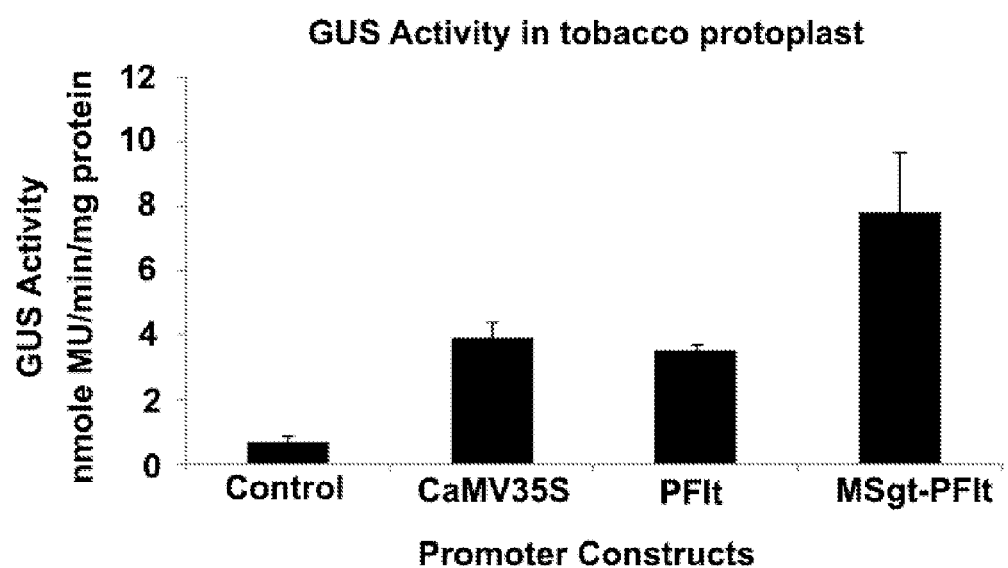

Transformed protoplast expressing CaMV35S, PFlt and MSgt-PFlt were incubated in 1 mM MUG (4-methyl-umbellifeiyl-D-glucuronide) at 37° C. for 30 min. to produce MU (7-Hydroxy-4-Methylcoumarin) for biochemical GUS estimation (Jefferson et al., 1987) and the result were presented in FIG. 11. We observed that pUPMSgt-PFlt promoter showed equivalent activity compared to that obtained from CaMV35S promoter in tobacco protoplast system.

Figure 12:
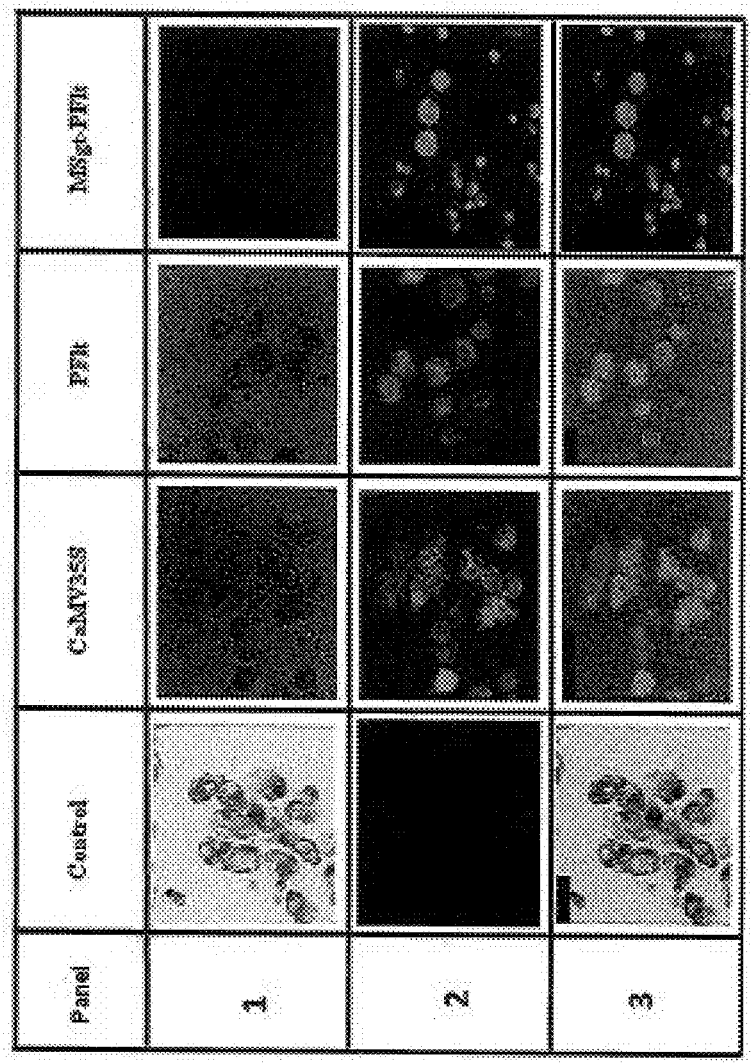

To further confirm the reporter gene (GUS) expression, in protoplast, we incubated the transformed protoplast expressing CaMV35S, PFlt and MSgt-PFlt promoter individually, in 55 mM ImaGene Green™ C12FDG1cU substrate (ImaGene Green™ GUS Gene Expression Kit; Invitrogen, Oregon, USA) as per kit's instructions and kept under vacuum infiltration for 10 min initially and then incubated at room temperature for 2-3 hrs in the dark. Fluorescence images of protoplast, transform with CaMV35S, PFlt promoter fragment and MSgt-PFlt promoter constructs were captured using a CLSM (TCS SP5; Leica, D 68165 Mannheim, Germany). The captured fluorescence images were presented in FIG. 12. For estimating GUS, the ImaGene Green™ treated transformed protoplast were excited with 488 diode laser (use of 495 nm UV laser may be more appropriate) and fluorescence emissions were collected between 500 and 515 nm with detector (PMT) gain set at 1150V. GUS localizations at cellular/tissue level were detected by green fluorescent lipophilic fluorescein derivative (5-dodecanoylaminofluorescein).

Figure 15:
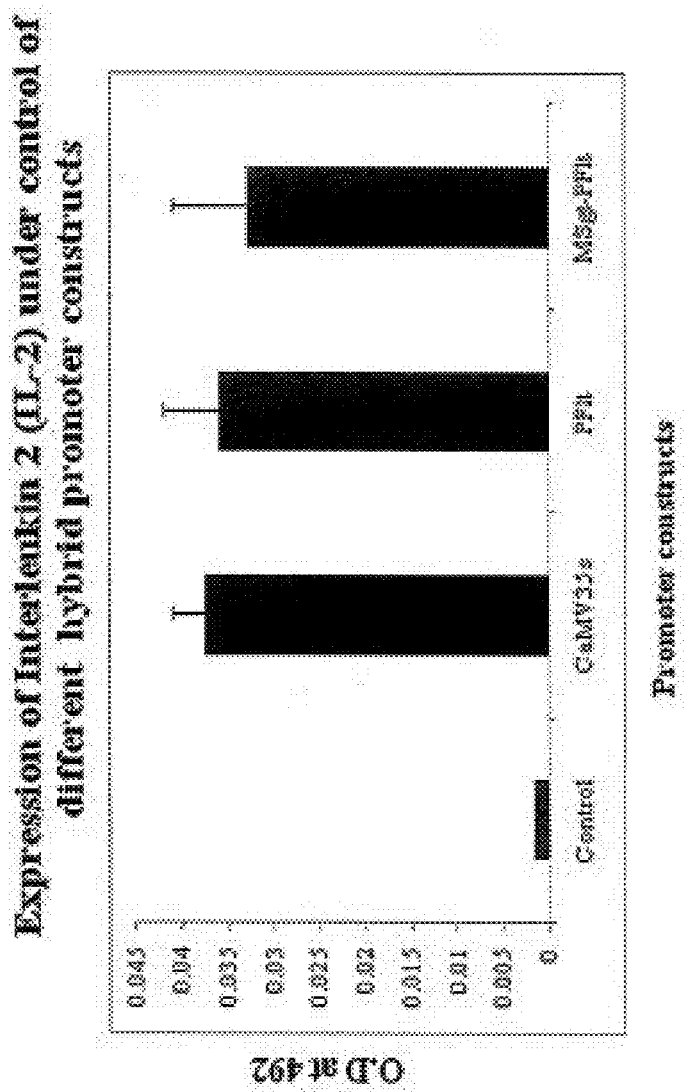
FIG. 15 shows expression of mammalian Interleukin-2 (IL-2) protein in tobacco protoplast under control of CaMV 35S, PFlt and MSgt-PFlt promoter.

ELISA of Protoplast Derived IL-2 Protein Driven by PFlt Promoter Fragment and MSgt-PFlt Promoter Constructs A 100 μl PBS containing 10 μg of protein extracts from protoplasts transformed with each of PFlt-IL-2 promoter fragment and MSgt-PFlt-IL-2 constructs were coated into a 96 well ELISA plate. The concentration of protoplast derived IL-2 was estimated following indirect ELISA protocol (Vazquez et al., 1996) using an anti-IL-2 antibody (Santacruz, USA) and the result obtained is presented in FIG. 15.

Example 7

Construction of Plant Expression Vectors with PFlt and MSgt-PFlt Promoters, Plant Transformation and Analysis of Transgenic Plants Promoter fragments PFlt (376 bp) and MSgt-PFlt (614 bp) were purified from corresponding pUC-clones and were subcloned into the plant expression vector pKYLX71GUS (Schardl et al., 1987; Dey and Maiti 1999) at its unique EcoR1 and HindIII sites that flank the promoter by replacing the CaMV35S promoter. Resulting plant expression vectors were designated pKPFlt-GUS and pK1VISgt-PFlt-GUS respectively.

Promoter constructs namely pKYLX-GUS (containing CaMV35S promoter), pKPFlt-GUS and pK1VISgt-PFlt-GUS were introduced into *Agrobacterium tumefaciens* strain C58C1:Pgv3850 by freeze thaw method. Tobacco plants (*Nicotiana tabacum* cv Samsun NN) were transformed with the engineered *Agrobacterium* as described earlier (Maiti et al., 1993). About 10 (ten) independent plant lines were generated for each construct. Regenerated Kanamycin-resistant plants were grown under greenhouse conditions (Temp-28±2° C., humidity-60 to 70%) until setting of seed. Seeds were collected from mature plant and germinated on Kanamycin antibiotic 300 mg per liter.

Figure 16:
FIG. 16 shows images of X-Gluc staining (Histochemical analysis) leaf petiole cross section of 21 days old transgenic plants expressing GUS under the control of CaMV35S, PFlt and MSgt-PFlt promoters, in accordance with the present disclosure, including the assay of Example 7.

5-bromo-4-chloro-3-indolyl-b-D-glucuronide (X-gluc), vacuum infiltrated under pressure for 10 mM followed by incubation at 37° C. overnight. Samples were then washed and fixed (in 50% ethanol, 7% acetic acid). The intensity of color development in different tissues was monitored and photographs were taken by using inverted Leica DM LS2 microscope at 4× magnification (FIG. 16).

Example 8

Figure 14:
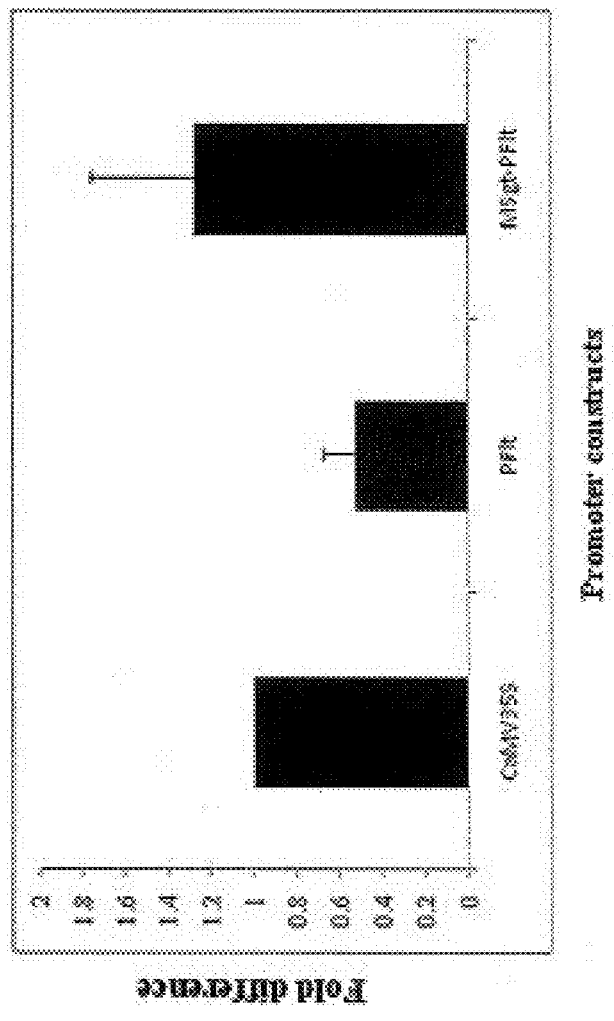

Reactions of qRT-PCR were performed as described earlier by Kumar et al., 2011. The cDNA was synthesized using RNA (DNaseI treated) isolated from transgenic tobacco plants expressing CaMV35S, PFlt and MSgt-PFlt promoter constructs individually using cDNA synthesis Kit (Fermentas, USA). The qRT-PCR for relative expression analysis was performed using the corresponding eDNA template (1:15 dilution) and SYBR Premix Ex TaqI'm II (Perfect Real Time, Takara Bio Inc., Japan) employing Opticon-2 Real-time PCR machine (MJ Research, Bio.-Rad; Model; CFD-3220). Gene specific primers for GUS were used at a concentration of 0.8 mmolar to get 95% efficiency. The absence of genomic DNA contamination was confirmed using minus-reverse-transcriptase controls. The Ct value for each reaction was obtained with the help of the software attached with the machine and fold changes in the transcript levels of each construct (considered for qRT-PCR) were presented (FIG. 14).

TABLE 2

Primer Sequences

| Sequence No. | Name of Constructs | Primer Sequence to amplify respective promoter in 5' to 3' direction |
|---|---|---|
| 16. | PFlt (forward) | GCGGGCGAATTCGTCAACGAGTTTTTACTTCGGACA |
| 17. | PFlt (reverse) | ATGCAGAAGCTTATGGCCGTGTCTTCTCGA |
| 18. | MSgt-PFlt (forward) | ACTGAATTCGTCGACAGCGGTAAAACAGGTGATTACT |
| 19. | MSgt-PFlt (reverse) | ATGCAGAAGCTTATGGCCGTGTCTTCTCGA |
| 12. | GUS (real time) (forward) | GATCGCGAAAACTGTGGAAT |
| 13. | GUS (real time) (reverse) | TAATGAGTGACCGCATCGAA |
| 14. | Interleukin 2 (forward) | GCGGGCTCGAGAACCATGGGTTACAGCATGCAGCTCGCA |
| 15. | Interleukin 2 (reverse) | ATGCAGTCTAGATCAGTGATGGTGATGGTGATGTTGAGGGCTTGTTGAGAT |

Analysis of GUS Expression in Transgenic Tobacco Plants

Figure 13:
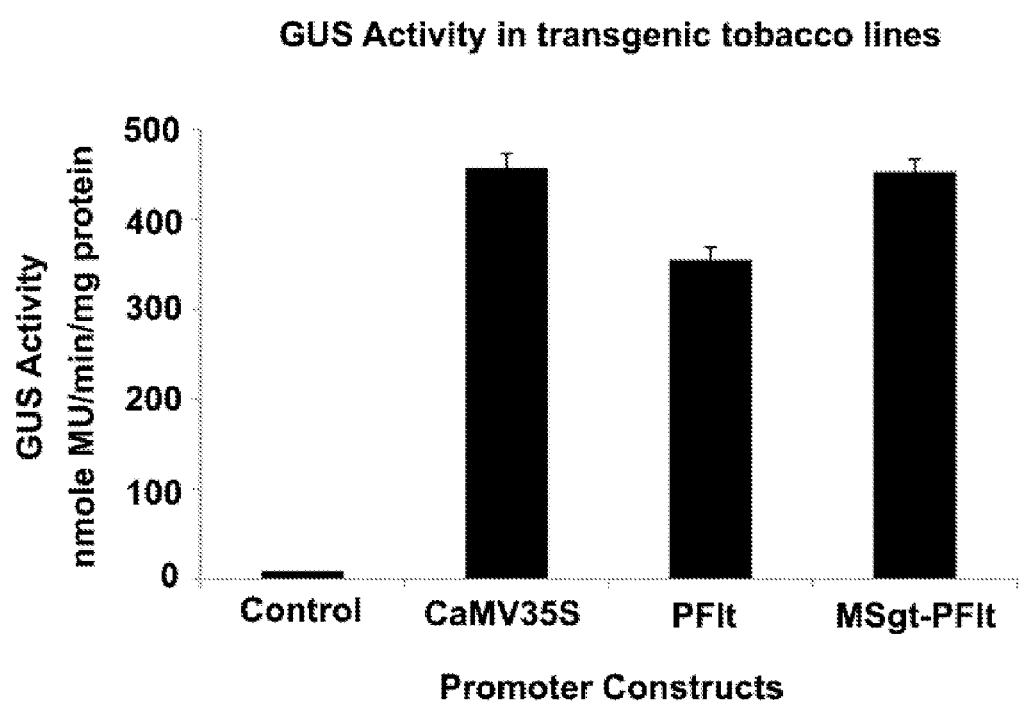

Independent tobacco transgenic lines were developed using CaMV35S, PFlt and MSgt-PFlt promoters as described earlier. Comparative GUS expression analyses were conducted using plant leaf (second from the top) extracts following protocol of Jefferson et al., 1987. The result obtained was presented in FIG. 13. Transgenic plants expressing the MSgt-PFlt promoter showed equivalent activity compared to the CaMV 35S promoter.

Transgenic plant sections expressing the GUS gene developed under each constructs were immersed into histochemical GUS staining buffer [100 mM NaPO$_4$, 0.5 mM K$_3$[Fe(CN)$_6$, 0.5 mM K$_4$[Fe(CN)$_6$], 10 mM EDTA, 1 mg/ml Information for SEQ ID No: 4 (FIG. 9)
 (i) Sequence characteristics: DNA (Genomic)
 (ii) Molecule type: Recombinant DNA
 (iii) Original source:
  (A) Organism: Peanut Chlortic Streak Virus (PC1SV) and Mirabilis Mosaic Virus (MMV).

** This promoter DNA clone MSgt-PFlt is being submitted to Microbial Type Culture Collection and Gene Bank (MTCC), Chandigarh, India under the Budapest treaty. All restrictions to the deposit will be revoked upon allowance of a patent covering the subject matter and the deposit will be replenished be if needed.

Example 9

Transient Assay of Recombinant Promoter in *Arabidopsis* Protoplast

Sterile young leaves of *Arabidopsis* plants were chopped under sterile condition and placed in MS agar media containing the following supplements: 1 mg/L of Naphthalene acetic acid (NAA), indole-3-acetic acid (IAA), 2,4-Dichlorophenoxyacetic acid (2,4-D) and 0.5 mg/L of 6-Benzylaminopurine (BAP). The plates were kept in dark at temperature 24° C. for one month for callus development. *Arabidopsis* callus were shred from plates to 30 ml enzyme solution containing 2% cellulose and 2% pectinase and incubated in dark at 50 rpm for 4 hours. After 4 hours, digested *Arabidopsis* cells were passed through a sieve, the flow through was collected and centrifuged at 200 g for 5 minutes. The pellet was suspended in 1 ml 0.6 M mannitol and 0.2% $CaCl_2$. Finally, the protoplasts were purified over 20% sucrose cushion and resuspended in a fresh medium containing 0.6 M mannitol and 0.2% $CaCl_2$. The isolated protoplast was counted with the help of haemocytometer.

Figure 17:
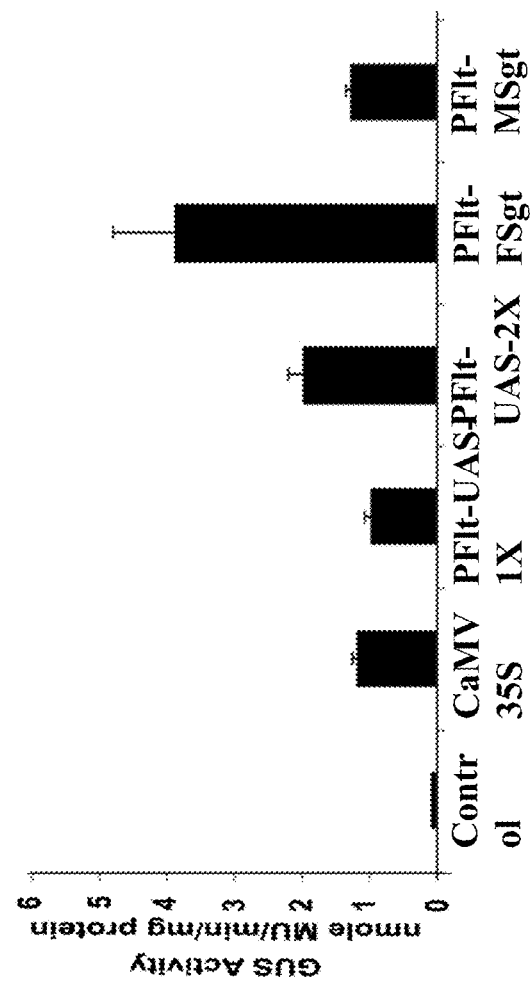
FIG. 17 is a graphing showing average GUS activities (nmole MU/min/mg protein) of CaMV35S, PFlt, PFLt-UAS-2X, FSgt-PFlt and MSgt-PFlt obtained from transformed *Arabidopsis* protoplast individually with corresponding standard deviations.

An aliquot of $10^5$ *Arabidopsis* protoplasts were electroporated with 10 μg plasmid DNA extracted individually from pUCPMA (vector control), pUCPMAGUS, PFltGUS, PFlt-UAS-2XGUS, FSgt-PFltGUS and MSgt-PFltGUS constructs following protocol described earlier and fluorimetric GUS assay was carried out following standard protocols (Bradford 1976; Jefferson et al. 1987). FIG. 17 presented the mean GUS activity obtained from four independent experiments for each of the above promoter constructs.

Example 10

Transient Agro-Infiltration Assay of Chimeric Promoters in *Solanum lycopersicum, Petunia Hybrida* and *Spinacia oleracea*

Figure 18:
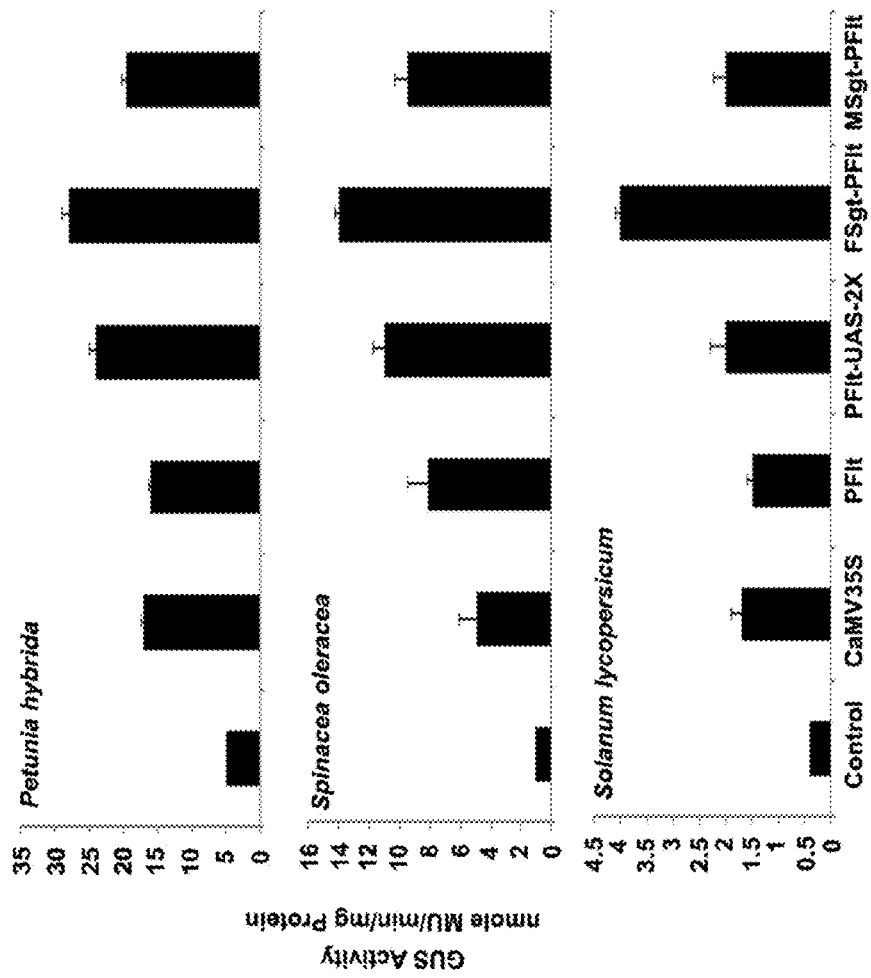
FIG. 18 are graphs showing transient GUS activities assay of CaMV35S, PFlt, PFLt-UAS-2X, FSgt-PFlt and MSgt-PFlt promoter constructs in three different plants system namely *Petunia hybrida, Spinacea oleracia* and *Solanum lycopersicum*, respectively.

*Agrobacterium tumefaciens* strain C58C1:pGV3850 was transformed with pKPFltGUS, pKPFlt-UAS-2XGUS, pKFSgt-PFltGUS and pKMSgt-PFltGUS constructs (pKYLX-GUS based) individually following the freeze thaw method as described earlier (Chen et al. 1994). Agrobacteria lines were grown as individual culture as described earlier. Leaves of *Spinacea oleracea, Petunia hybrida* and *Solanum lycopersicum* (var. Samsun NN) were mechanically infused with each *Agrobacterium* constructs individually as described (Imogen et al. 2006). Quantitative measurements of the GUS activity were performed 3-4 days post infusion following standard protocol. FIG. 18 presented the mean GUS activity (obtained from four independent experiments) for each of the promoter constructs in above mentioned plant with respective standard deviations.

Example 11

Histochemical Staining of Germinating Seeds, Whole Seedlings and Fluorescent Imaging of Floral Organs Longitudinal cross-sections of germinating seeds expressing pKYLXGUS, pKPFltGUS, pKPFlt-UAS-2XGUS, pKFSgt-PFltGUS and pKMSgt-PFltGUS promoter constructs individually were performed at different time-points Viz. 0, $2^{nd}$, $4^{th}$ and $8^{th}$ day of post germination using a Cryostat (Modell CM1850-1-1, Leica). Longitudinal sections of transgenic seed and whole seedlings of transgenic plant (21 days old) expressing pKYLXGUS, pKPFltGUS, pKPFlt-UAS-2XGUS, pKFSgt-PFltGUS and pKMSgt-PFltGUS constructs were immersed separately into histochemical GUS staining buffer [100 mM $NaPO_4$, 0.5 mM $K_3[Fe(CN)_6]$, 0.5 mM $K_4[Fe(CN)_6]$, 10 mM EDTA, 1 mg/ml 5-bromo-4-chloro-3-indolyl-b-D-glucuronide (X-gluc)], vacuum infiltrated for 10 min followed by incubation at 37° C. for overnight. Treated samples were subsequently washed and kept in fixing solutions (50% ethanol, 7% acetic acid). The intensities of blue color development in different tissues were recorded using Leica DM LS2 microscope (Inverted) at 10× magnification. (FIG. 19).

Detailed histochemical expression analysis of the reporter gene (GUS) in different sections of floral organs/parts of transgenic plant expressing pKYLXGUS, pKPFltGUS, pKPFlt-UAS-2XGUS, pKFSgt-PFltGUS and pKMSgt-PFltGUS constructs was carried out individually in presence of 55 mM ImaGene Green™ C12FDG1cU substrate (ImaGene Green™ GUS Gene Expression Kit; Invitrogen, Oregon, USA) as per Kit's instructions. Subsequently, treated samples were kept in dark after vacuum infiltration for 10 minutes. Fluorescence images of the ImaGene Green™ treated floral sections were captured using a CLSM (TCSSP5; Leica, D-68165 Mannheim, Germany) and GUS localizations at cellular/tissue level were detected. (FIG. 20) Intensities of green fluorescence obtained from different 50/60 ROIs (regions of interest) of transgenic floral organs for individual promoter construct were recorded using 'LAS-AF' analytical software and average intensity obtained from different floral organ/tissue were measured (FIG. 21).

Example 12

Spatial Distribution of GUS Activities Obtained from CaMV35S, CaMV35S2, PFlt, PFlt-UAS-2X, FSgt-PFlt and MSgt-PFlt Promoters On an average, 8-11 independent plant lines were generated for each construct and maintained under standard greenhouse conditions till setting of seeds. Seeds were collected from each plant line under each construct and germinated on MS plate supplemented with 300 mg Kan/liter; segregation analysis for each line was determined (with $Kan^R:Kan^S=3:1$). Kanamycin-resistant seedlings ($T_1$ generation) under each construct with appropriate segregation ratio were used for further analysis. Leaf, root and stem protein of transgenic seedling (21 days old) expressing above promoter constructs individually were extracted and the average GUS activity was measured according to the standard protocols (Bradford, 1976; Jefferson et al., 1987). FIG. 22 presented the mean promoter activity for each of the promoter construct with respective standard deviation.

Example 13

SA and ABA Treatment

Transgenic tobacco seeds expressing pKYLX (Control), pKYLX, pKYLXGUS, $pKYLXGUS35S^2$, pKPFltGUS, pKPFlt-UAS-2XGUS, pKFSgt-PFltGUS and pKMSgt-PFltGUS constructs were germinated on half MS plate (containing 300 mg/liter Kanamycin) and allowed to grow under tissue culture conditions as described earlier (Kumar et al. 2012). The whole transgenic seedlings (21 days old) under each constructs were treated individually in the presence of 150 μM SA (pH 6.8) and ABA (pH 6.8) for a period of 0-24 h, respectively.

After treatments, GUS activity from SA- and ABA-treated root, leaf, stem portion of seedlings under each of the above mentioned promoter constructs were measured (Bradford 1976; Jefferson et al. 1987). The data obtained as a mean of four independent experiments in FIG. 9 with respective standard deviation presented in FIG. 23.

The following are the accession numbers of your cultures deposited in Microbial Type Culture Collection and Gene Bank Institute of Microbial Technology (MTCC), Sector 39-A, Chandigarh—160036, INDIA, under Budapest treaty.
  E. coli (TG1)—pUC PFlt-UAS-2X=MTCC 5825
  E. coli (TG1)—pUC FSgt-PFlt=MTCC 5826
  E. coli (TG1)—pUC MSgt-PFlt=MTCC 5827

It will now be clear that the present invention provides features and advantages not found in prior known promoters. Further, one of ordinary skill in the art will recognize that aspects of the present disclosure can be modified using routine techniques consistent with the present disclosure.

REFERENCES CITED

Throughout this document, various references are mentioned. All references, including those listed below, are hereby incorporated by reference.

References Cited

1. Bestwick R K, Kellogg J A Synthetic Hybrid Tomato E4/E8 Plant Promoter—U.S. Pat. No. 6,118,049.
2. Bhattacharyya S, Dey N, Maiti 1 B (2002) Analysis of cis-sequence of subgenomic transcript promoter from the Figwort mosaic virus and comparison of promoter activity with the Cauliflower mosaic virus promoters in monocot and dicot cells. Virus Res 90: 47-62.
3. Bhullar S, Chakravarthy S, Advani S, Datta S, Pental D, et al. (2003) Strategies for development of functionally equivalent promoters with minimum sequence homology for transgene expression in plants: cis-elements in a novel DNA context versus domain swapping. Plant Physiol 132: 988-998.
4. Bradford M M (1976) A rapid and sensitive method for quantitation of microgram quantities of protein utilizing the principle of protein-dye binding. Anal Biochem 72: 248-254.
5. Comai L, Moran P, Maslyar D (1990) Novel and useful properties of a chimeric plant promoter combining CaMV 35S and MAS elements. Plant Mol Biol 15: 373-381.
6. Chen H, Nelson R S, Sherwood J L (1994) Enhanced recovery of transformants of Agrobacterium tumefaciens after freeze-thaw transformation and drug selection. BioTechniques 16: 664-668, 670
7. Dey N, Maiti 1 B (1999) Structure and promoter/leader deletion analysis of mirabilis mosaic virus (MMV) full-length transcript promoter in transgenic plants. Plant Mol Biol 40: 771-782.
8. Goodrich J A, Tjian R (2010) Modes of transcriptional regulation: Unexpected roles for core promoter recognition factors in cell-type-specific transcription and gene regulation. Nat Rcv Genetics 11: 549-558.
9. Imogen A S, John R, Anne K, Chris H (2006) Rapid, transient expression of fluorescent fusion proteins in tobacco plants and generation of stably transformed plants. Nature Prot 10: 286
10. Jefferson R A, Kavanagh T A, Bevan M W (1987) GUS fusions: beta-glucuronidase as a sensitive and versatile gene fusion marker in higher plants. EMBO J 6: 3901-3907.
11. Kumar D, Patro S, Ranjan R, Sahoo D K, Maiti I B, et al. (2011) Development of useful recombinant promoter and its expression analysis in different plant cells using Confocal Laser Scanning Microscopy. PLoS ONE 6(9): e24627doi: 10.1371/journal.pone. 0024627.
12. Kumar D, Patro S, Ghosh J, Das A, Maiti I B, Dey N (2012) Development of a salicylic acid inducible minimal sub-genomic transcript promoter from Figwort mosaic virus with enhanced root- and leaf-activity using TGACG motif rearrangement. Gene 503: 36-47
13. Lee L Y, Kononov M E, Bassuner B, Frame B R, Wang K, et al. (2007) Novel Plant Transformation Vectors Containing the Superpromoter. Plant Physiol 145: 1294-1300.
14. Maiti I B, Gowda S, Kiernan J, Ghosh S K, Shepherd R J (1997) Promoter/leader deletion analysis and plant expression vectors with Figwort Mosaic Virus (FMV) full-length transcript (Flt) promoter containing single and double enhancer domains. Transgenic Res 6: 143-156.
15. Ni M, Cui D, Einstein J, Narasimhulu S, Vergara C E (1995) Strength and tissue specificity of chimeric promoters derived from the octopine and mannopine synthase genes. The Plant J 7: 661-676.
16. Ranjan R, Patro S, Kumari S, Kumar D, Dey N, et al. (2011) Efficient chimeric promoters derived from full-length and sub-genomic transcript promoters of Figwort mosaic virus (FMV). Journal of Biotechnology 152: 58-62.
17. Rushton P J, Reinstadler A, Lipka V, Lippok B, Somssich I E (2002) Synthetic plant promoters containing defined regulatory elements provides novel insights into pathogen- and wound-induced signaling. Plant Cell 14: 749-762.
18. Vazquez F, Gonzalez E A, Garabal J I, ValdeiTama S, Blanco J, et al. (1996) Development and evaluation of an ELISA to detect Escherichia coli 1(88 (F44) fimbrial antibody levels. J Med Microbial 44: 453-463.
19. Venter M (2007) Synthetic Promoters: genetic control through cis engineering. Trends in Plant Sci 12: 118-124.
20. Venter M, Botha F C (2010) Synthetic promoter engineering. In Plant Developmental Biology-Biotechnological Perspective Pua E-C, Davey M R, eds. Springer-Verlag Berlin Heidelberg 2: 393-414.

The invention claimed is:

1. An isolated non-naturally occurring DNA molecule, comprising a Peanut Chlortic Streak Virus (PC1SV) full-length transcript promoter (Flt) fragment, and a Mirabilis Mosaic Virus (MMV) subgenomic transcript promoter (Sgt) fragment, comprising the sequence of SEQ ID NO: 4.

2. The isolated DNA molecule of claim 1, wherein
the PC1SV full-length transcript promoter fragment comprises a fragment between coordinates −353 to +24, and
the MMV Sgt promoter fragment comprises a fragment between coordinates −356 to −125.

3. The isolated DNA molecule of claim 2, wherein the MMV Sgt fragment is ligated to the 5' end of the PC1SV Flt fragment.

4. The isolated DNA molecule of claim 1, having activity that is at least 35, 40, 45, 50, 55, 60, 65, 70, 75, 80, 85, 90, 95, 96, 97, 98, or 99% as compared to the activity of a CaMV35S promoter.

* * * * *

SEQUENCE LISTING

```
<160> NUMBER OF SEQ ID NOS: 19

<210> SEQ ID NO 1
<211> LENGTH: 376
<212> TYPE: DNA
<213> ORGANISM: Artificial Sequence
<220> FEATURE:
<223> OTHER INFORMATION: combined sequence from PFlt and UAS
```

```
<400> SEQUENCE: 1
agtttttact tcggacagtc aaaaatgagt ttaacttctc agccgaggta aaacaagaaa      60
tatgcttacg tctacagagg gatttctctg aagatcatgt tgccagcta tgcgaacaat     120 catcgggaga tcttgagcca atcaaagagg agtgatgtag acctaaagca ataatggagc    180
catgacgtaa gggcttacgc ccatacgaaa taattaaagg ctgatgtgac ctgtcggtct    240
ctcagaacct ttacttttta tatttggcgt gtattttta atttccacgg caatgacgat    300
gtgacctgtg catccgcttt gcctataaat aagttttagt ttgtattgat cgacacgatc    360
gagaagacac ggccat                                                    376

<210> SEQ ID NO 2
<211> LENGTH: 686
<212> TYPE: DNA
<213> ORGANISM: Artificial Sequence
<220> FEATURE:
<223> OTHER INFORMATION: combined promotor from PF1t and UAS

<400> SEQUENCE: 2
agtttttact tcggacagtc aaaaatgagt ttaacttctc agccgaggta aaacaagaaa      60
tatgcttacg tctacagagg gatttctctg aagatcatgt tgccagctat gcgaacaatc    120
atcgggagat cttgagccaa tcaaagagga gtgatgtaga cctaaagcaa taatggagcc    180
atgacgtaag ggcttacgcc catacgaaat aattaaaggc tgatgtgacc tgtcggtctc    240
tcagaacctt tactttttat atttggcgtg tatttttaaa tttccacggc aatgacgagg    300
tgacccaacg agtttttact tcggacagtc aaaaatgagt ttaacttctc agccgaggta    360
aaacaagaaa tatgcttacg tctacagagg gatttctctg aagatcatgt tgccagcaa    420 tgcgaacaat catcgggaga tcctgagcca atcaaagagg agtgatgtag acctaaagca    480
ataatggagc catgacgtaa gggcttacgc ccatacgaaa taattaaagg ctgatgtgac    540
ctgtcggtct ctcagaacct ttacttttta tatttggcgt gtattttaa atttccacgg    600 caatgacgat gtggcctgtg catccgcttt gcctataaat aagttttagt ttgtattgat    660
cgacacgatc gagaagacac ggccat                                         686

<210> SEQ ID NO 3
<211> LENGTH: 593
<212> TYPE: DNA
<213> ORGANISM: Artificial Sequence
<220> FEATURE:
<223> OTHER INFORMATION: combined promoter clone FSgt and PF1

<400> SEQUENCE: 3
ttacagtaag aactgataac aaaaatttta cttatttcct tagaattaat cttaaaggtg      60
atagtaaaca aggacgatta gtccgttggc aaaattggtt cagcaggtat caatttgatg    120
tcgaacatct tgaaggtgta aaaaacgttt tagcagattg cctcacgaga gattttaatg    180
cttaaaaacg taagcgctga cgtatgattt cccaacgagt ttttacttcg gacagtcaaa    240
aatgagttta acttctcagc cgaggtaaaa caagaaatat gcttacgtct acagagggat    300
ttctctgaag atcatgtttg ccagcaatgc gaacaatcat cgggagatcc tgagccaatc    360
aaagaggagt gatgtagacc taaagcaata atggagccat gacgtaaggg cttacgccca    420
tacgaaataa ttaaaggctg atgtgacctg tcggtctctc agaacctta ctttttatat    480 ttggcgtgta tttttaaatt tccacggcaa tgacgatgtg gcctgtgcat ccgctttgcc    540
tataaataag ttttagtttg tattgatcga cacgatcgag aagacacggc cat          593
```

-continued

<210> SEQ ID NO 4
<211> LENGTH: 614
<212> TYPE: DNA
<213> ORGANISM: Artificial Sequence
<220> FEATURE:
<223> OTHER INFORMATION: combined promoter clone from MSgt and PFlt

<400> SEQUENCE: 4

```
cggtaaaaca ggtgattact aaatttagta tttatctaac ccctgtttgt tttacagtca     60
ggacagataa tgtaaatctt ttaaaaggat ttatgaataa aaagattact ggtgacagta    120
aacagggaag gctaataaga tggcaaatgt ggttttcaca ttacaccttt aaggtggacc    180
acctaaaagg agaacaaaat gtgctggctg attatctcac cagagaattc ccccaacgag    240
tttttacttc ggacagtcaa aaatgagttt aacttctcag ccgaggtaaa acaagaaata    300
tgcttacgtc tacagaggga tttctctgaa gatcatgttt gccagcaatg cgaacaatca    360
tcgggagatc ctgagccaat caaagaggag tgatgtagac ctaaagcaat aatggagcca    420
tgacgtaagg gcttacgccc atacgaaata attaaaggct gatgtgacct gtcggtctct    480
cagaaccttt actttttata tttggcgtgt atttttaaat ttccacggca atgacgatgt    540
ggcctgtgca tccgctttgc ctataaataa gttttagttt gtattgatcg acacgatcga    600
gaagacacgg ccat                                                      614
```

<210> SEQ ID NO 5
<211> LENGTH: 376
<212> TYPE: DNA
<213> ORGANISM: Peanut chlorotic streak virus

<400> SEQUENCE: 5

```
agtttttact tcggacagtc aaaaatgagt ttaacttctc agccgaggta aaacaagaaa     60
tatgcttacg tctacagagg gatttctctg aagatcatgt ttgccagcta tgcgaacaat    120
catcgggaga tcttgagcca atcaaagagg agtgatgtag acctaaagca ataatggagc    180
catgacgtaa gggcttacgc ccatacgaaa taattaaagg ctgatgtgac ctgtcggtct    240
ctcagaacct ttacttttta tatttggcgt gtatttttaa atttccacgg caatgacgat    300
gtgacctgtg catccgcttt gcctataaat aagttttagt ttgtattgat cgacacgatc    360
gagaagacac ggccat                                                    376
```

<210> SEQ ID NO 6
<211> LENGTH: 36
<212> TYPE: DNA
<213> ORGANISM: Artificial Sequence
<220> FEATURE:
<223> OTHER INFORMATION: promotor sequence

<400> SEQUENCE: 6

```
gcgggcgaat tcgtcaacga gtttttactt cggaca                               36
```

<210> SEQ ID NO 7
<211> LENGTH: 30
<212> TYPE: DNA
<213> ORGANISM: Artificial Sequence
<220> FEATURE:
<223> OTHER INFORMATION: primer sequence

<400> SEQUENCE: 7

```
atgcagaagc ttatggccgt gtcttctcga                                     30
```

-continued

<210> SEQ ID NO 8
<211> LENGTH: 36
<212> TYPE: DNA
<213> ORGANISM: Artificial Sequence
<220> FEATURE:
<223> OTHER INFORMATION: primer seqeunece

<400> SEQUENCE: 8
gcgggcgaat tcgtcaacga gttttttactt cggaca                36

<210> SEQ ID NO 9
<211> LENGTH: 30
<212> TYPE: DNA
<213> ORGANISM: Artificial Sequence
<220> FEATURE:
<223> OTHER INFORMATION: primer sequence

<400> SEQUENCE: 9
atgcagaagc ttatggccgt gtcttctcga            30

<210> SEQ ID NO 10
<211> LENGTH: 37
<212> TYPE: DNA
<213> ORGANISM: Artificial Sequence
<220> FEATURE:
<223> OTHER INFORMATION: primer

<400> SEQUENCE: 10
cccgaattcg tcgactttac agtaagaact gataaca                37

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
atgcagaagc ttatggccgt gtcttctcga            30

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gatcgcgaaa actgtggaat             20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
taatgagtga ccgcatcgaa             20

<210> SEQ ID NO 14
<211> LENGTH: 39
<212> TYPE: DNA
<213> ORGANISM: Artificial Sequence
<220> FEATURE:
<223> OTHER INFORMATION: primer

```
<400> SEQUENCE: 14
gcgggctcga gaaccatggg ttacagcatg cagctcgca                             39

<210> SEQ ID NO 15
<211> LENGTH: 51
<212> TYPE: DNA
<213> ORGANISM: Artificial Sequence
<220> FEATURE:
<223> OTHER INFORMATION: primer

<400> SEQUENCE: 15
atgcagtcta gatcagtgat ggtgatggtg atgttgaggg cttgttgaga t              51

<210> SEQ ID NO 16
<211> LENGTH: 36
<212> TYPE: DNA
<213> ORGANISM: Artificial Sequence
<220> FEATURE:
<223> OTHER INFORMATION: primer

<400> SEQUENCE: 16
gcgggcgaat tcgtcaacga gtttttactt cggaca                                36

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
atgcagaagc ttatggccgt gtcttctcga                                       30

<210> SEQ ID NO 18
<211> LENGTH: 37
<212> TYPE: DNA
<213> ORGANISM: Artificial Sequence
<220> FEATURE:
<223> OTHER INFORMATION: primer

<400> SEQUENCE: 18
actgaattcg tcgacagcgg taaaacaggt gattact                               37

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
atgcagaagc ttatggccgt gtcttctcga                                       30
```